United States Patent
Martin et al.

(10) Patent No.: US 9,247,938 B2
(45) Date of Patent: Feb. 2, 2016

(54) SUTURE FASTENING DEVICE

(75) Inventors: David T. Martin, Milford, OH (US); James A. Woodard, Jr., Mason, OH (US); Carl J. Shurtleff, Mason, OH (US); Kevin A. Larson, South Lebanon, OH (US); Mark J. Bookbinder, Blue Ash, OH (US); John L. Stammen, Cincinnati, OH (US)

(73) Assignee: Ethicon Endo-Surgery, inc., Cincinnati, OH (US)

( * ) Notice: Subject to any disclaimer, the term of this patent is extended or adjusted under 35 U.S.C. 154(b) by 424 days.

(21) Appl. No.: 13/467,333

(22) Filed: May 9, 2012

(65) Prior Publication Data

US 2012/0290005 A1     Nov. 15, 2012

Related U.S. Application Data

(60) Provisional application No. 61/484,395, filed on May 10, 2011.

(51) Int. Cl.
*A61B 17/04* (2006.01)
*A61B 17/062* (2006.01)
*A61B 17/29* (2006.01)

(52) U.S. Cl.
CPC ........... *A61B 17/062* (2013.01); *A61B 17/0469* (2013.01); *A61B 17/0483* (2013.01); *A61B 2017/2926* (2013.01)

(58) Field of Classification Search
CPC ........... A61B 17/0469; A61B 17/0483; A61B 17/062; A61B 2017/2926
USPC .................. 606/144, 151, 232, 213, 233, 139
See application file for complete search history.

(56) References Cited

U.S. PATENT DOCUMENTS

| | | | | |
|---|---|---|---|---|
| 5,556,402 | A * | 9/1996 | Xu | 606/147 |
| 6,056,771 | A * | 5/2000 | Proto | 606/222 |
| 6,071,289 | A * | 6/2000 | Stefanchik et al. | 606/147 |
| 7,628,796 | B2 * | 12/2009 | Shelton et al. | 606/144 |
| 8,236,010 | B2 * | 8/2012 | Ortiz et al. | 606/142 |
| 2003/0171761 | A1 * | 9/2003 | Sancoff et al. | 606/139 |
| 2005/0096699 | A1 * | 5/2005 | Wixey et al. | 606/232 |
| 2010/0100125 | A1 | 4/2010 | Mahadevan | |
| 2011/0313433 | A1 | 12/2011 | Woodard, Jr. et al. | |
| 2012/0037686 | A1 * | 2/2012 | Hessler | 227/175.1 |

(Continued)

OTHER PUBLICATIONS

U.S. Appl. No. 13/449,494, filed Apr. 18, 2012, Woodard, Jr. et al.

*Primary Examiner* — Thomas McEvoy
*Assistant Examiner* — Julie A Szpira
(74) *Attorney, Agent, or Firm* — Frost Brown Todd LLC

(57) ABSTRACT

An apparatus is operable to secure suture fasteners to sutures to eliminate the need to tie knots in the sutures. The apparatus comprises a shaft, an end effector disposed at the distal end of the shaft, and a suture fastener removably secured to the end effector. The end effector may include a pivoting jaw or a suture cutter. The suture fastener may be secured to one, two, or more strands of suture. The apparatus may include several suture fasteners and may secure those fasteners to one or more sutures in a serial fashion without having to remove the apparatus from the patient for reloading. A plurality of fasteners may be arranged within the apparatus in an end-to-end configuration. The suture fastener may include an inner fastener member and an outer fastener member, and may capture one or more strands of suture between the inner and outer fastener members.

17 Claims, 33 Drawing Sheets

(56) References Cited

U.S. PATENT DOCUMENTS

2012/0123471 A1* 5/2012 Woodard et al. .............. 606/223
2012/0150199 A1* 6/2012 Woodard et al. .............. 606/147
2012/0283748 A1* 11/2012 Ortiz et al. .................... 606/139

* cited by examiner

SUTURE FASTENING DEVICE

PRIORITY

This application claims priority to U.S. Provisional Application Ser. No. 61/484,395, filed May 10, 2011, entitled "Laparoscopic Suturing Devices and Methods," the disclosure of which is incorporated by reference herein.

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparoscopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Additional suturing instruments are disclosed in U.S. Pat. No. 7,628,796, entitled "Surgical Suturing Apparatus with Anti-Backup System," issued Dec. 8, 2009, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. Pub. No. 2011/0313433, entitled "Laparoscopic Suture Device with Asynchronous In-Line Needle Movement," filed Jun. 9, 2011, and issued as U.S. Pat. No. 9,168,037 on Oct. 27, 2015, the disclosure of which is incorporated by reference herein; U.S. patent application No. 13/449,494, entitled "Laparoscopic Suturing Instrument with parallel Concentric Shaft Pairs," filed Apr. 18, 2012, published as U.S. Pat. Publication No. 2013/0282027 on Oct. 24, 2013, the disclosure of which is incorporated by reference herein; and U.S. Provisional Patent Application No. 61/355,832, entitled "Laparoscopic Suture Device," filed Jun. 17, 2010, now expired, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, now abandoned, the disclosure of which is incorporated by reference herein; U.S. Provisional Application Serial No. 61/413,680, filed Nov. 15, 2010, entitled "Custom Needle for Suture Instrument," now expired, the disclosure of which is incorporated by reference herein; U.S. patent application Ser. No. 13/295,186, entitled "Needle for Laparoscopic Suturing Instrument," filed on Nov. 14, 2011, published as U.S. Patent Publication No. 2012/0123471 on May 17, 2012, and issued as U.S. Pat. No. 9,125,646 on Sep. 8, 2015, the disclosure of which is incorporated by reference herein; and U.S. patent application Ser. No. 13/295,203, entitled "Laparoscopic Suturing Instrument with Dual-Action Needle Graspers," filed on Nov. 14, 2011, now U.S. Pat. No. 8,702,732 issued Apr. 22, 2014, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
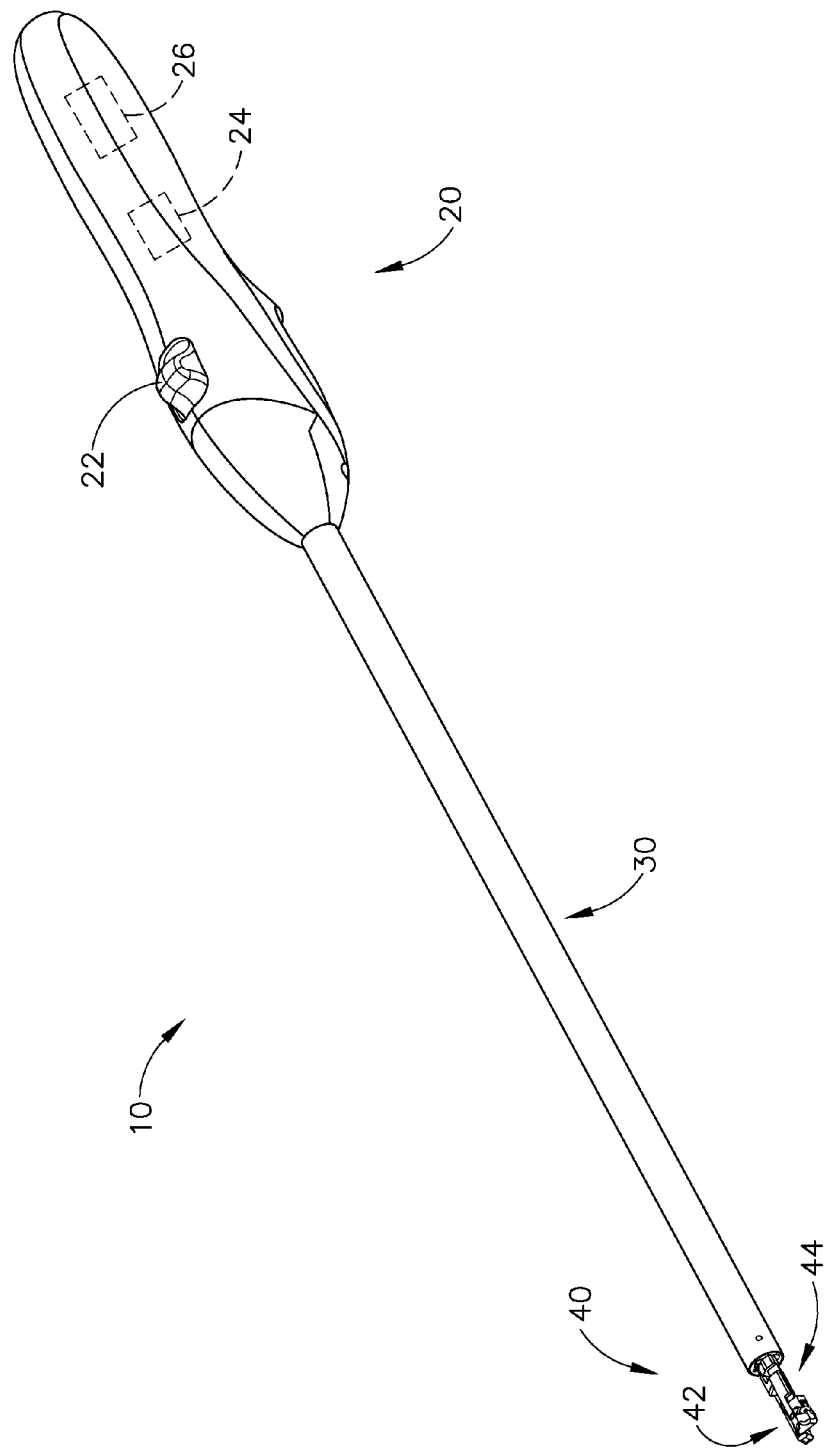
FIG. 1 depicts a perspective view of an exemplary laparoscopic suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Suturing Instrument

Figure 2:
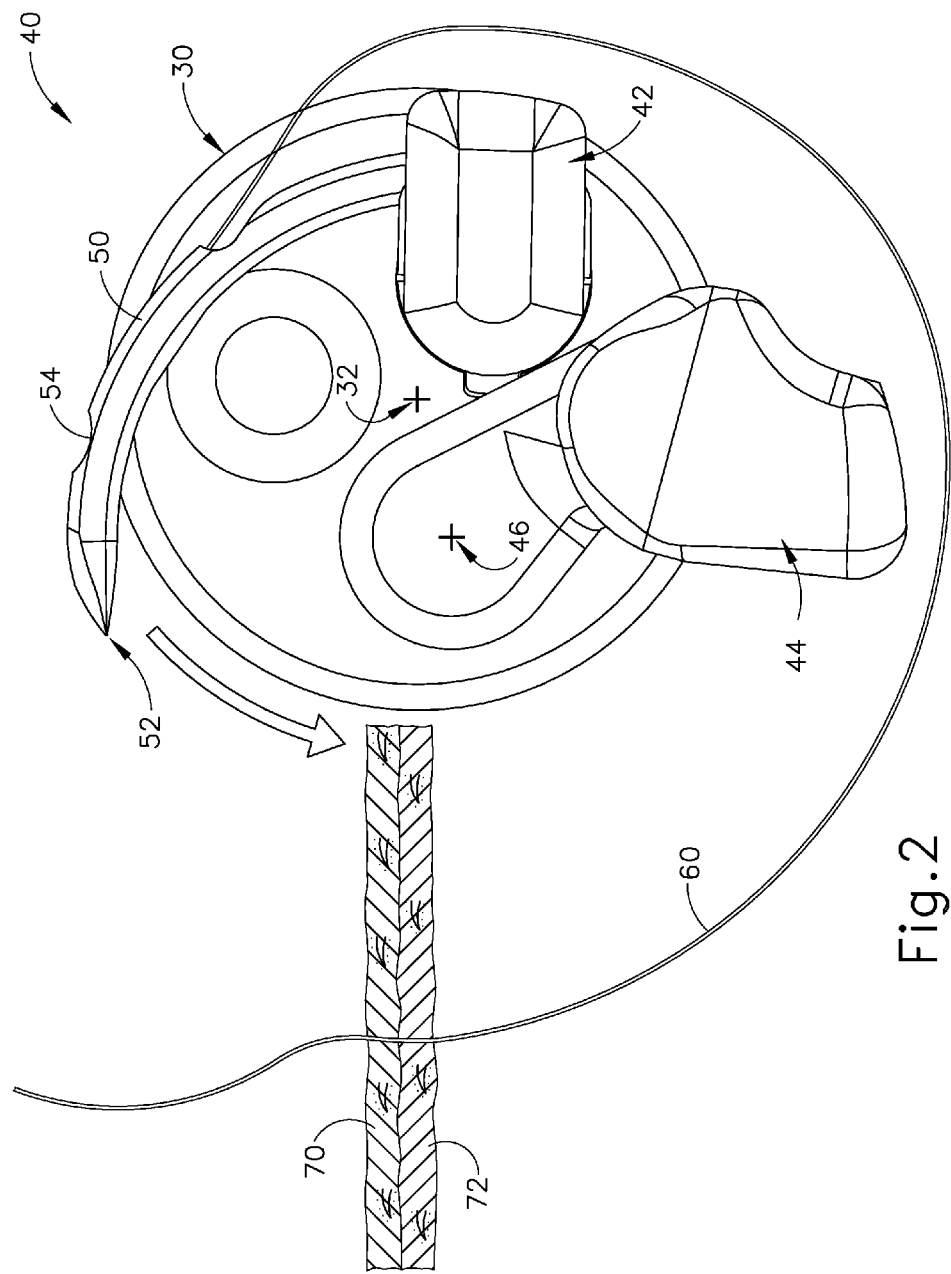
FIG. 2 depicts an end view of the end effector of the suturing instrument of FIG. 1.
Figure 3A:
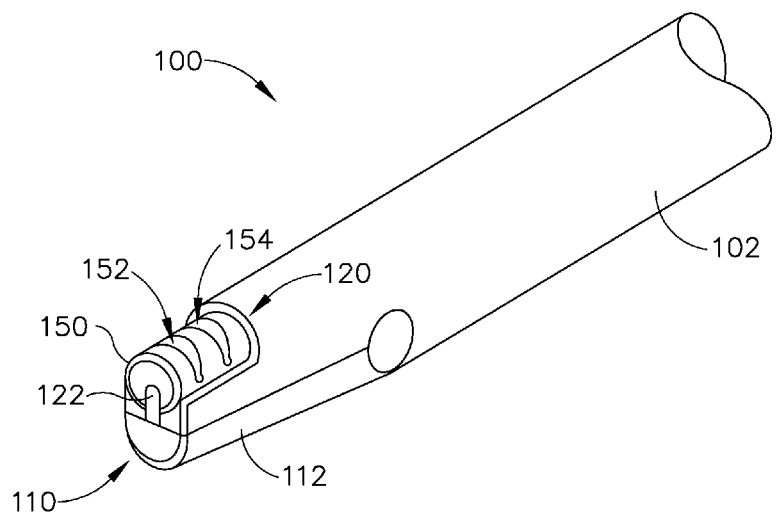
FIG. 3A depicts a perspective view of an end effector of an exemplary suture fastening instrument, with a jaw in a closed position.
Figure 3B:
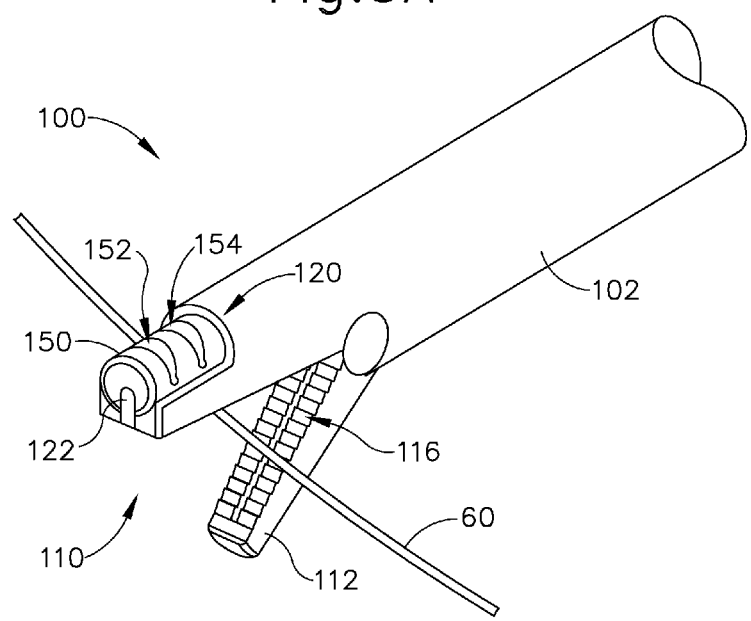
FIG. 3B depicts a perspective view of the end effector of FIG. 3A, with the jaw in an open position to receive a suture strand.
Figure 3C:
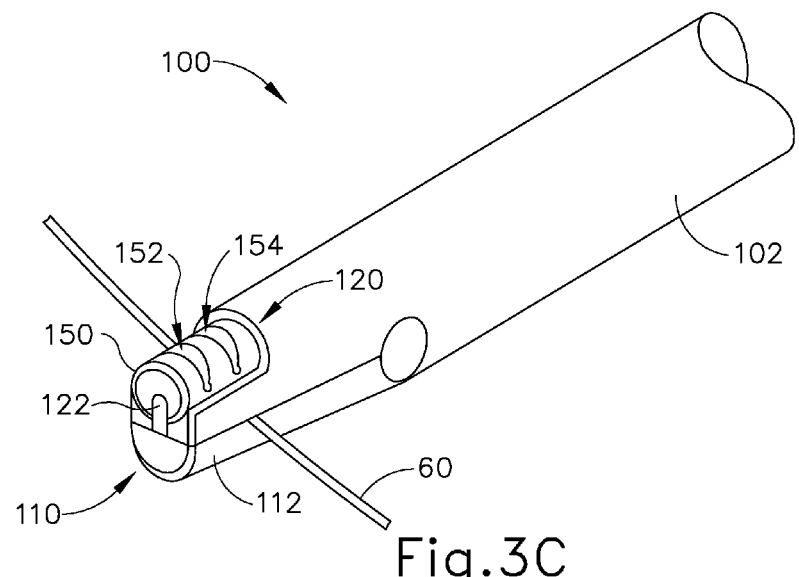
FIG. 3C depicts a perspective view of the end effector of FIG. 3A, with the jaw closed on the suture strand to sever the suture strand.
Figure 3D:
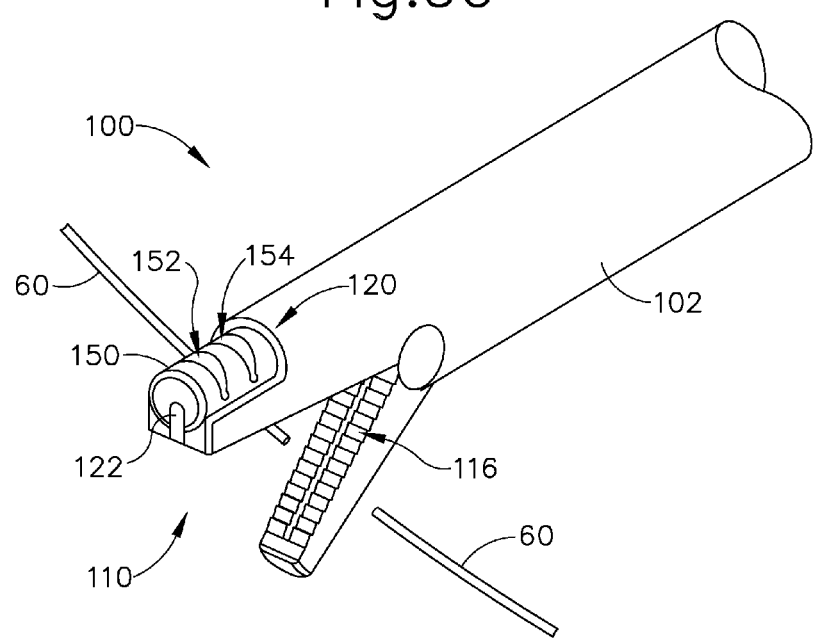
FIG. 3D depicts a perspective view of the end effector of FIG. 3A, with the jaw opened to release the severed suture strand.
Figure 4A:
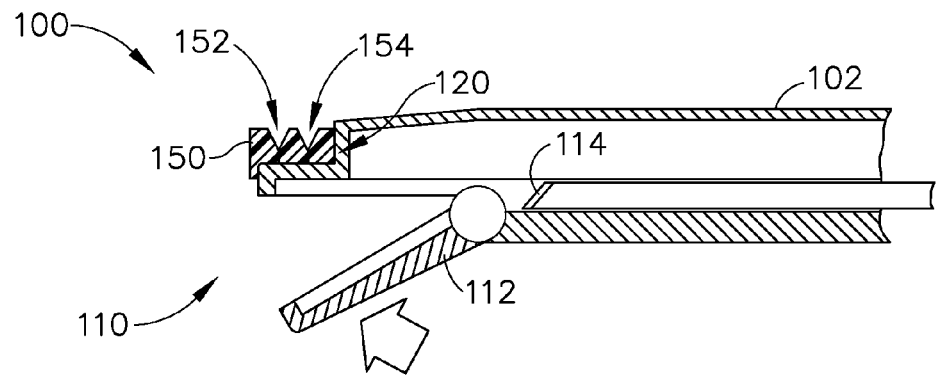
FIG. 4A depicts a side cross-sectional view of the end effector of FIG. 3A, with the jaw in the open position and a cutter in a proximal position.
Figure 4B:
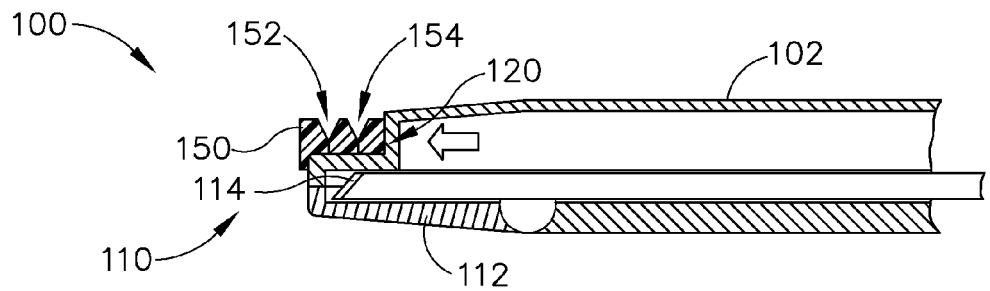
FIG. 4B depicts a side cross-sectional view of the end effector of FIG. 3A, with the jaw in the closed position and the cutter in a distal position.
Figure 4C:
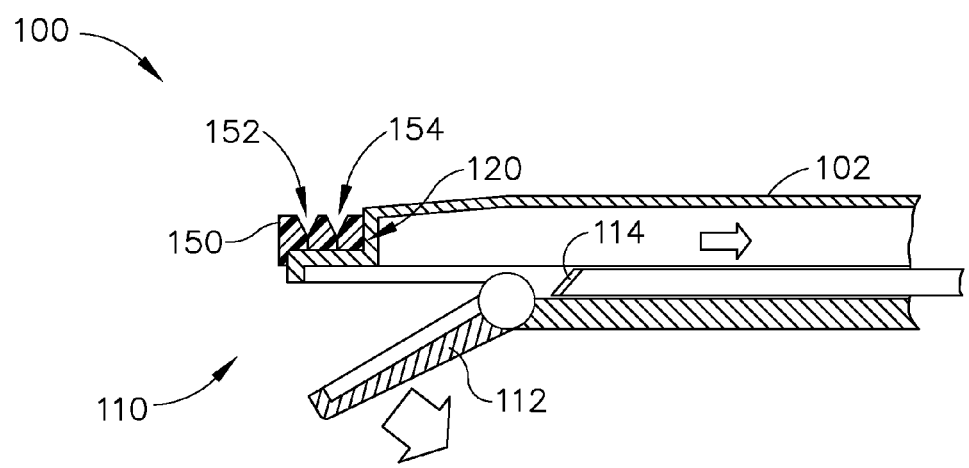
FIG. 4C depicts a side cross-sectional view of the end effector of FIG. 3A, with the jaw back in the open position and the cutter back in the proximal position.

FIGS. 1-2 show an exemplary laparoscopic suturing instrument (10), which may be used to suture tissue in numerous kinds of surgical procedures. Instrument (10) of this example includes a handle portion (20), a shaft assembly (30) extending distally from handle portion (20), and an end effector (40) at the distal end of shaft assembly (30). Handle portion (20) includes a rocker (22), an integral power source (26), and a motor (24) in communication with the integral power source (26). Rocker (22) is operable to selectively activate motor (24) to actuate features of end effector (40) as will be described in greater detail below. Integral power source (26) comprises a rechargeable battery in the present example, though it should be understood that any other suitable internal or external power source may be used.

Shaft assembly (30) of the present example has an outer diameter sized to permit shaft assembly (30) to be inserted through a conventional trocar (not shown). Shaft assembly (30) also has a length sized to permit end effector (40) to be positioned at a surgical site within a patient while also allowing handle portion (20) to be manipulated by a user (e.g., a surgeon) from a location outside the patient when shaft assembly (30) is disposed in a trocar. Of course, shaft assembly (30) need not necessarily be dimensioned for use through a trocar. For instance, instrument (10) may be used and/or configured for use in open surgical procedures.

End effector (40) of the present example includes a first grasping arm (42) and a second grasping arm (44). Each grasping arm (42, 44) extends along a respective axis that is parallel to yet offset from the center axis (32) of shaft assembly (30). First grasping arm (42) is substantially straight while second grasping arm (44) includes a dogleg bend near its distal end, as best seen in FIG. 2. Each arm (42, 44) includes a respective pair of jaws that are operable to selectively grasp and release a suturing needle (50). Arms (42, 44) are also operable to alternatingly throw and catch suturing needle (50) along an arcuate path in a plane that is substantially perpendicular to the longitudinal axis (32) defined by shaft assembly (30). Alternatively, arms (42, 44) may be configured to alternatingly throw and catch needle (50) along a path in a plane that is substantially parallel to the longitudinal axis (32) defined by shaft assembly (30); or along some other path. First grasping arm (42) maintains a fixed rotational position relative to shaft assembly (30) while second grasping arm (44) is rotatable about its longitudinal axis (46) during operation of instrument (10) in the present example.

Of course, the above described components and operabilities of suturing instrument (10) are merely exemplary. Other suitable components, features, configurations, and operabilities that may be incorporated into a suturing instrument (10) will be apparent to those of ordinary skill in the art in view of the teachings herein. By way of example only, suturing instrument (10) may be constructed and/or operable in accordance with at least some of the teachings of U.S. patent application No. 13/449,494, published as U.S. Patent Publication No. 2013/0282027 on Oct. 24, 2013, the disclosure of which is incorporated by reference herein; U.S. Provisional Patent Application No. 61/355,832, now expired, the disclosure of which is incorporated by reference herein; U.S. Pub. No. 2011/0313433, now U.S. Pat. No. 9,168,037, issued on Oct. 27, 2015, the disclosure of which is incorporated by reference herein; and/or any other reference cited herein.

As shown in FIG. 2, needle (50) of this example includes a sharp tip (52) and grasping regions (54) configured for grasping by arms (42, 44). In particular, grasping regions (54) comprise scallops in the present example, though it should be understood that grasping regions (54) may have various other configurations. A suture (60) is secured to a mid-region of needle (50). The configuration and relationship of suture (60) and needle (50) provides an exit of suture (60) from needle (50) at an angle that is generally tangent to or oblique relative to the curvature of needle (50). While the example described below includes just a single strand of suture extending from the needle, it should be understood that two or more strands may extend from the needle (e.g., double leg suture, etc.). As yet another merely illustrative example, suture (60) may be secured to a blunt end (not shown) of needle (50) instead of being secured to a mid-region of needle (50). In still other versions, both ends of needle (50) are sharp. It should also be understood that needle (50) may be straight instead of curved in some versions. By way of example only, needle (50) may be constructed in accordance with at least some of the teachings of U.S. Provisional Application No. 61/413,680, now expired; U.S. Patent Application Nos. 13/295,186, published as U.S. Pub. No. 2012/0123471 on May 17, 2012, now U.S. Pat. No. 9,125,646, issued on Sep. 8, 2015, and 13/295,203, now U.S. Pat. No. 8,702,732, issued on Apr. 22, 2014; U.S. Pat. No. 6,056,771; and/or U.S. Pub. No. 2010/0100125, published Apr. 22, 2010, now abandoned. Still other suitable configurations for needle (50) will be apparent to those of ordinary skill in the art in view of the teachings herein.

FIG. 2 shows end effector (30) positioned to drive needle (50) and suture (60) through layers (70, 72) of tissue. Layers (70, 72) are shown in an apposed configuration in the present example, such that layers (70, 72) are positioned in parallel but separate planes. However, it should be understood that instrument (10) may also be used to drive needle (50) and suture (60) through portions of tissue that are substantially coplanar with each other. For instance, substantially coplanar portions of tissue on both sides of an incision may have severed edges placed alongside each other, and instrument (10) may be used to drive needle (50) and suture (60) through the tissue to close the incision with stitches, with the severed edges of the tissue being held together. Other suitable settings in which instrument (10) may be used will be apparent to those of ordinary skill in the art in view of the teachings herein.

Referring back to FIG. 2, a user may rotate the entire end effector (30) counterclockwise about axis (32) to drive needle (50) through layers (70, 72) of tissue. The user may then activate motor (24) to rotate arm (44) clockwise about axis (46), to position the open jaws of arm (44) about grasping region (54) of needle (50). The user may then further activate motor (24) to close the jaws of arm (44) about needle (50) to grasp needle with arm (44); then open the jaws of arm (42) to release needle (50) from arm (42). With control of needle (50) thus being transitioned from arm (42) to arm (44), the user may further activate motor (24) to rotate arm (44) counter-clockwise about axis (46), to pull the rest of needle (50) and suture (60) through layers (70, 72) of tissue. The user may then pull end effector (30) away from the tissue to pull additional length of suture (60) through the tissue; then activate motor (24) to rotate arm (44) clockwise about axis (46) to transition control of needle from arm (44) back to arm (42). Next, the user may rotate the entire end effector (30) clockwise about axis (32) to reposition needle (50) for subsequent insertion of needle (50) through the tissue. The above process may be repeated a number of times to create a desirable number of stitches.

In some instances, suture (60) may be secured in place by one or more knots. Such knots may prevent suture (60) from being pulled through tissue. Various examples of instruments and suture fastener devices that may be used to secure suture (60) relative to the tissue (e.g., similar to a clip) in lieu of using knots, to thereby secure the stitches in place, will be described in greater detail below while still other examples of such instruments and devices will be apparent to those of ordinary skill in the art in view of the teachings herein. It should be understood that numerous versions of the suture fasteners described below are configured to provide functionality similar to a knot, such that the suture fasteners simply prevent one or more strands of suture (60) from being pulled through tissues. Numerous versions of the suture fasteners described below remain positioned adjacent to tissue once deployed; and such suture fasteners do not penetrate tissue and are not otherwise embedded within tissue. Some other variations may include one or more features that are operable to at least partially penetrate tissue and/or otherwise embed within tissue. It should also be understood that the below described instruments and devices may be used in conjunction with various other kinds of suturing instruments (10) and needles (50), etc., such that the inventors' contemplation is not limited to instrument (10) and needle (50) described above.

II. Exemplary Suture Fastening and Cutting Instrument with Double Strand Grasping Fasteners FIGS. 3A-4C show an exemplary instrument (100) that is operable to cut a suture (60) and apply fasteners (150) to strands (62, 64) of suture (60). Instrument (100) of this example includes a shaft (102) and an end effector (110) at the distal end of shaft (102). Shaft (102) and end effector (110) of the present example are sized and configured to fit through a conventional trocar for use in a minimally invasive surgical procedure, though it should be understood that shaft (102) and end effector (110) may have any other size and configuration. It should also be understood that numerous kinds of manual and/or automated control features may be provided at the proximal end of shaft (102) to control end effector (110). By way of example only, a handle including one or more triggers, dials, knobs, sliders, buttons, and/or other kinds of user input features may be located at the proximal end of shaft (102). In addition or in the alternative, a handle or other kind of body at the proximal end of shaft (102) may include one or more motors (e.g., electrical, pneumatic, etc.), one or more linear actuators (e.g., solenoids, pneumatic cylinders, etc.), gearing, and/or other kinds of drive components operable to drive end effector (110). Similarly, various kinds of components may be provided within shaft (102) to communicate motion to end effector (110), including but not limited to rods, beams, cables, etc. Various kinds of suitable components and features that may be provided within shaft (102) and at the proximal end of shaft (102) to operate end effector (110) will be apparent to those of ordinary skill in the art in view of the teachings herein.

End effector (110) of the present example includes a pivoting jaw (112) and a fastener applier (120). Pivoting jaw (112) is operable to pivot toward and away from fastener applier (120), as seen in the series depicted in FIGS. 3A-4C. As also seen in the series depicted in FIGS. 3A-4C, a translating cutter (114) is operable to translate longitudinally through a channel (116) formed in jaw (112) to sever a suture (60) that is captured by jaw (112). In some other versions, cutter (114) is provided as a stationary blade that is integral with jaw (112), such that cutter (114) pivots unitarily with jaw (112) toward and away from fastener applier (120). In some such versions, a surface underneath fastener applier (120) acts as a cutting board. Alternatively, a feature underneath fastener applier (120) may cooperate with cutter (114) to provide a shearing action with cutter (114). It should also be understood that pivoting jaw (112) and cutter (114) are each merely optional. For instance, some variations of end effector (110) may include pivoting jaw (112) but lack cutter (114). As another merely illustrative variation, end effector (110) may lack both pivoting jaw (112) and cutter (114).

Fastener applier (120) is configured to receive and actuate a fastener (150). Fastener (150) of the present example includes a pair of slit (152, 154) configured to receive respective strands of suture (60). In some versions, at least part of fastener (150) is malleable, such that fastener (150) may selectively clamp down on strands of suture (60) to effectively lock fastener (150) to suture (60) in a manner similar to a split shot sinker on a fishing line. As another merely illustrative example, slit (152, 154) may include features enabling fastener (150) to selectively lock to suture (60) without requiring malleability. Various suitable features that may be used to lock fastener (150) to suture (60) will be apparent to those of ordinary skill in the art in view of the teachings herein. By way of example only, at least part of fastener (150) may be constructed from one or more of titanium, stainless steel, PEEK plastic, polyethylene, and/or absorbable suture material (e.g., vicryl, PDS, etc.), among various other kinds of materials, including combinations of materials. It should also be understood that any other fastener described herein may be constructed from any one or more of the above-listed materials, among other types of materials. Various suitable kinds of materials and combinations of materials will be apparent to those of ordinary skill in the art in view of the teachings herein.

Fastener applier (120) also includes a pivoting stop member (122) that is operable to engage a distal end of each fastener (150). Stop member (122) is operable to pivot toward and away from fastener (150), such that stop member (122) may prevent distal movement of fastener (150) when stop member (122) is pivoted to an orientation that is transverse to the longitudinal axis of shaft (102); and such that stop member (122) permits distal movement of fastener (150) when stop member (122) is pivoted to an orientation that is substantially parallel to the longitudinal axis of shaft (102). Stop member (122) may also be configured to assist in ejecting fastener (150) from fastener applier (120) when stop member (122) is pivoted to an orientation that is substantially parallel to the longitudinal axis of shaft (102). In versions where fastener (150) is malleable, stop member (122) may provide an anvil to compress fastener (150) against. For instance, an actuator within shaft (102) may bear distally on fastener (150) to compress fastener (150) against stop member (122). It should also be understood that fastener applier (120) may be operable to selectively only lock one slit (132, 134) at a time. For instance, fastener applier (120) may include an insert member (not shown) that is selectively disposed in slit (154) when slit (152) is compressed to a locked configuration, with the insert member preventing slit (154) from being compressed to a locked configuration when slit (152) is compressed to a locked configuration. Alternatively, fastener applier (120) may simply lock both slit (152, 154) simultaneously. Other suitable features and configurations for fastener applier (120) and fasteners (150) will be apparent to those of ordinary skill in the art in view of the teachings herein.

Figure 5:
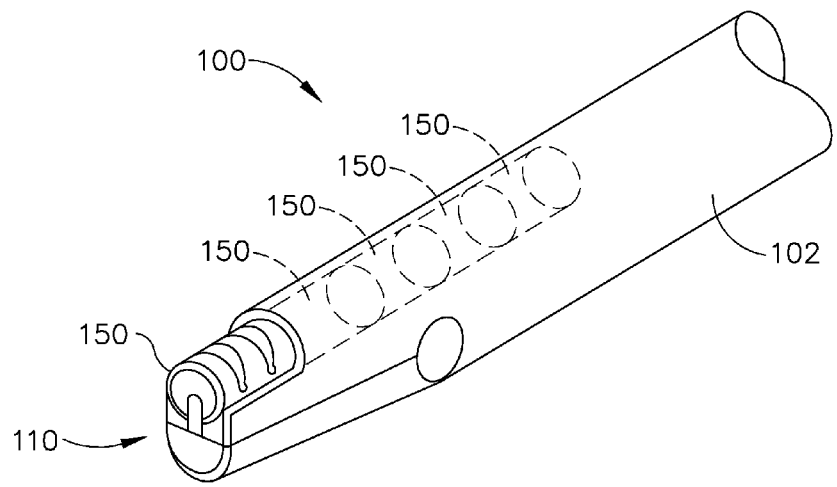
FIG. 5 depicts a perspective view of the end effector of FIG. 3A with a series of suture fasteners stacked in an end-to-end configuration within the shaft of the suture fastening instrument.
Figure 6:
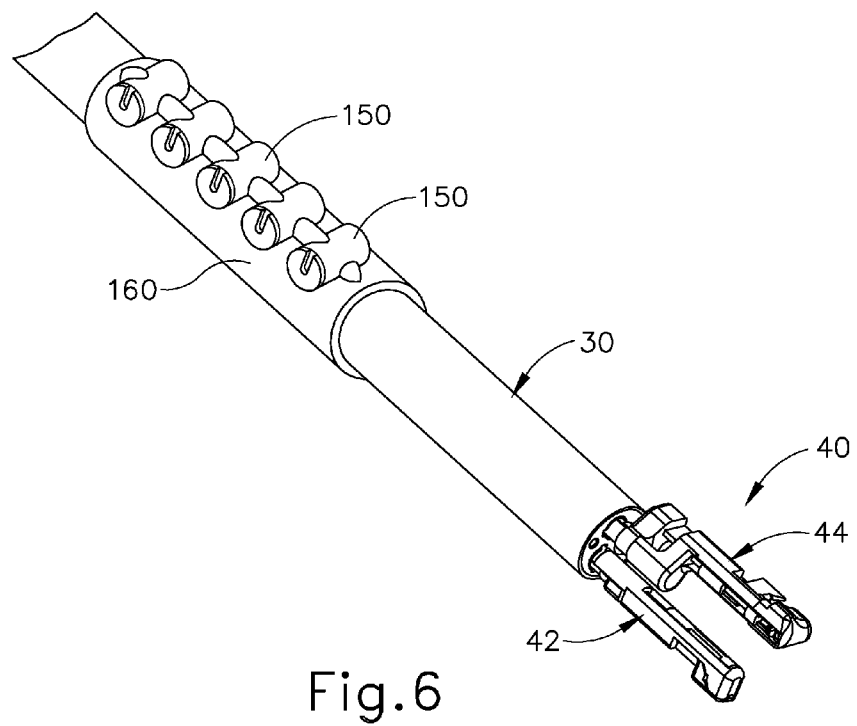
FIG. 6 depicts a perspective view of a suture fastener carrying sheath positioned on the shaft of the suturing instrument of FIG. 1.

In the example shown in FIGS. 3A-3D, end effector (110) includes just a single fastener (150) disposed in fastener applier (120). In the example shown in FIG. 5, a plurality of fasteners (150) are positioned in an end-to-end configuration, such that after a distal-most fastener is released from fastener applier (120), the next fastener (150) in line will move distally (e.g., under a resilient bias from a spring, etc.) to the position previously occupied by the released fastener (120). This configuration may enable fastener applier (120) to apply several fasteners (150) before having to be reloaded. In the event that fastener applier (120) needs to be reloaded, this may be accomplished within the patient, leaving end effector (110) disposed in the patient via a trocar; or end effector (110) may be pulled from the patient to reload fastener applier (120) outside of the patient. As another merely illustrative variation, the additional fasteners (150) may be positioned along an axis that is parallel to yet offset from the longitudinal axis passing through fastener applier (120). For instance, shaft (102) may include a feature similar to the tubular magazine of a shotgun to store and dispense fasteners (150) from. In some versions such as those shown in FIGS. 3A-3D where instrument (100) just includes a single fastener (150) at a time, additional fasteners (150) may be carried by a cartridge or sheath (160) disposed on shaft assembly (30) of instrument (10), as shown in FIG. 6. Fastener applier (120) may be operable to selectively load fasteners (150) from sheath (160) within the patient. In other words, end effector (110) need not be extracted from the patient in order to reload fastener applier (120). Sheath (160) may be introduced through a trocar and then secured to shaft assembly (30) within the patient. As another merely illustrative alternative, sheath (160) may be secured to shaft assembly (30) before the two are together inserted into the patient (e.g., via a trocar or other port or via an open incision, etc.).

Figure 7A:
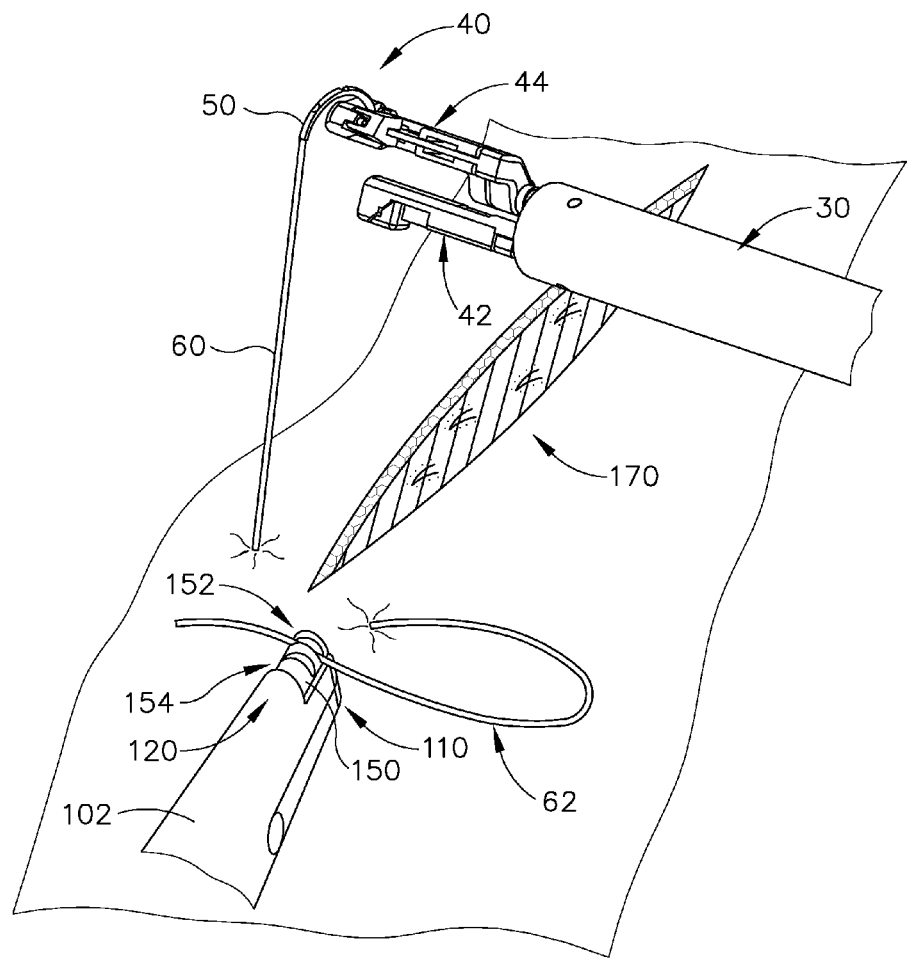
FIG. 7A depicts a perspective view of the suturing instrument of FIG. 1 and the end effector of FIG. 3A adjacent to an incision site, with the suturing instrument of FIG. 1 having pulled a suture through tissue, with part of the suture strand received in a suture fastener of the end effector of FIG. 3A, and with the suture strand in a substantially slack state.
Figure 7B:
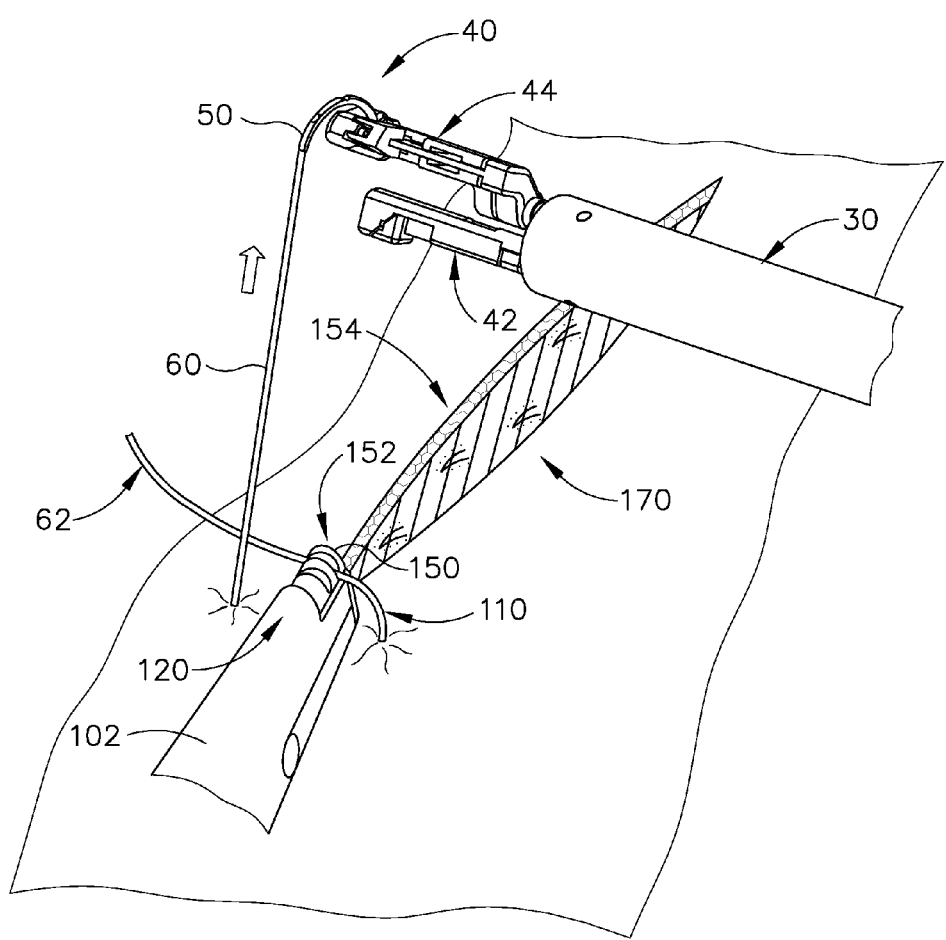
FIG. 7B depicts a perspective view of the suturing instrument of FIG. 1 and the end effector of FIG. 3A adjacent to an incision site, with the suture strand in a substantially tensioned state.
Figure 7C:
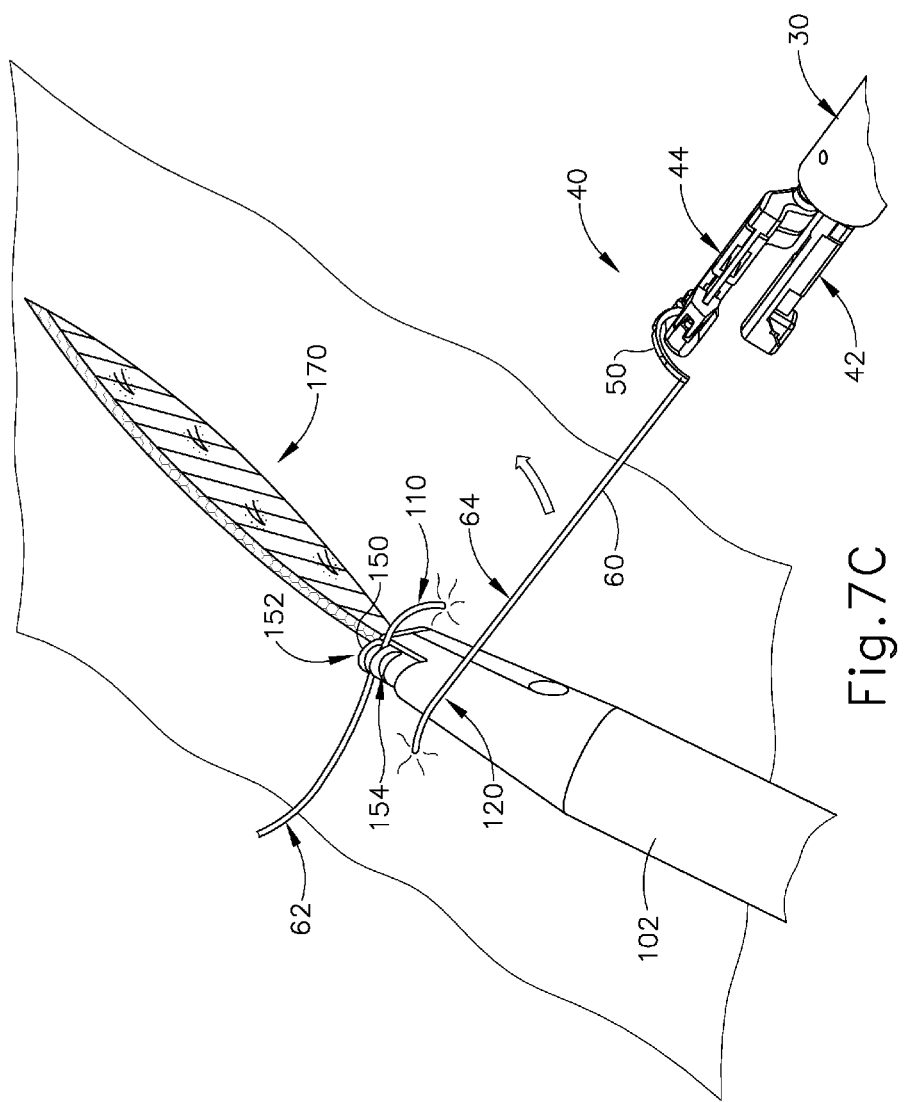
FIG. 7C depicts a perspective view of the suturing instrument of FIG. 1 and the end effector of FIG. 3A adjacent to an incision site, with the suturing instrument of FIG. 1 having been moved to wrap the suture over a portion of the end effector of FIG. 3A.
Figure 7D:
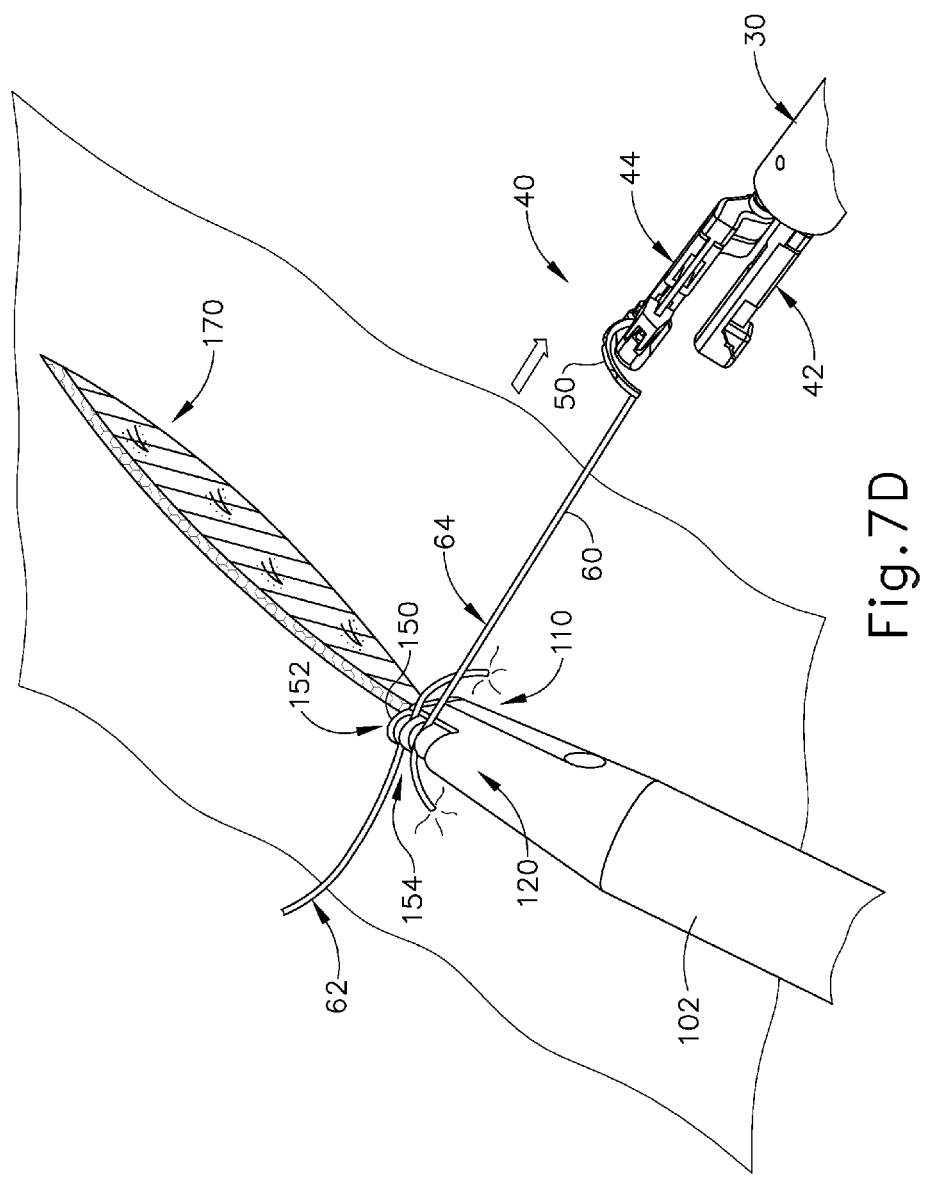
FIG. 7D depicts a perspective view of the suturing instrument of FIG. 1 and the end effector of FIG. 3A adjacent to an incision site, with the suturing instrument of FIG. 1 having been further moved to position another portion of the suture strand in the suture fastener of the end effector of FIG. 3A.
Figure 7E:
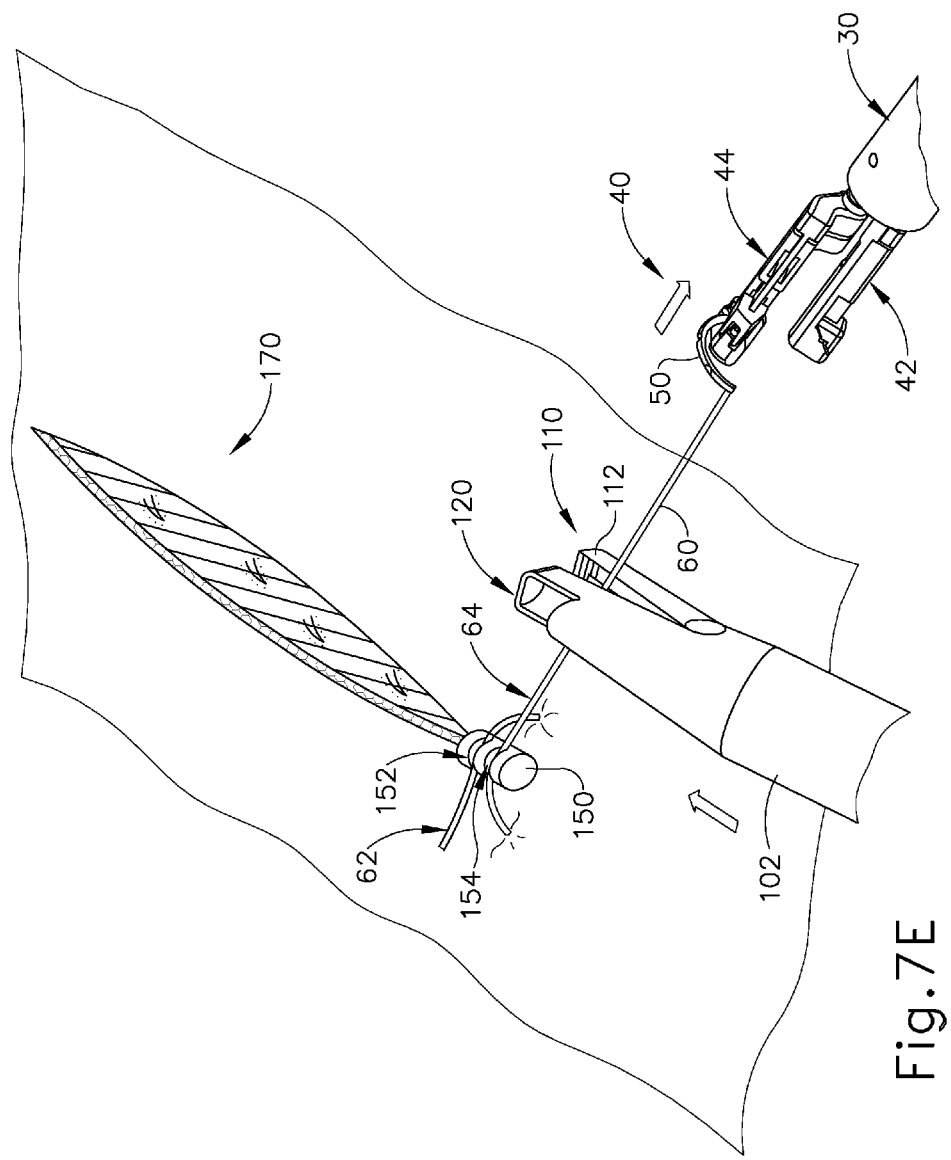
FIG. 7E depicts a perspective view of the suturing instrument of FIG. 1 and the end effector of FIG. 3A adjacent to an incision site, with the end effector of FIG. 3A having secured the suture fastener to the suture and with the end effector of FIG. 3A being positioned to sever the suture while the suturing instrument of FIG. 1 holds the suture in tension.
Figure 7F:
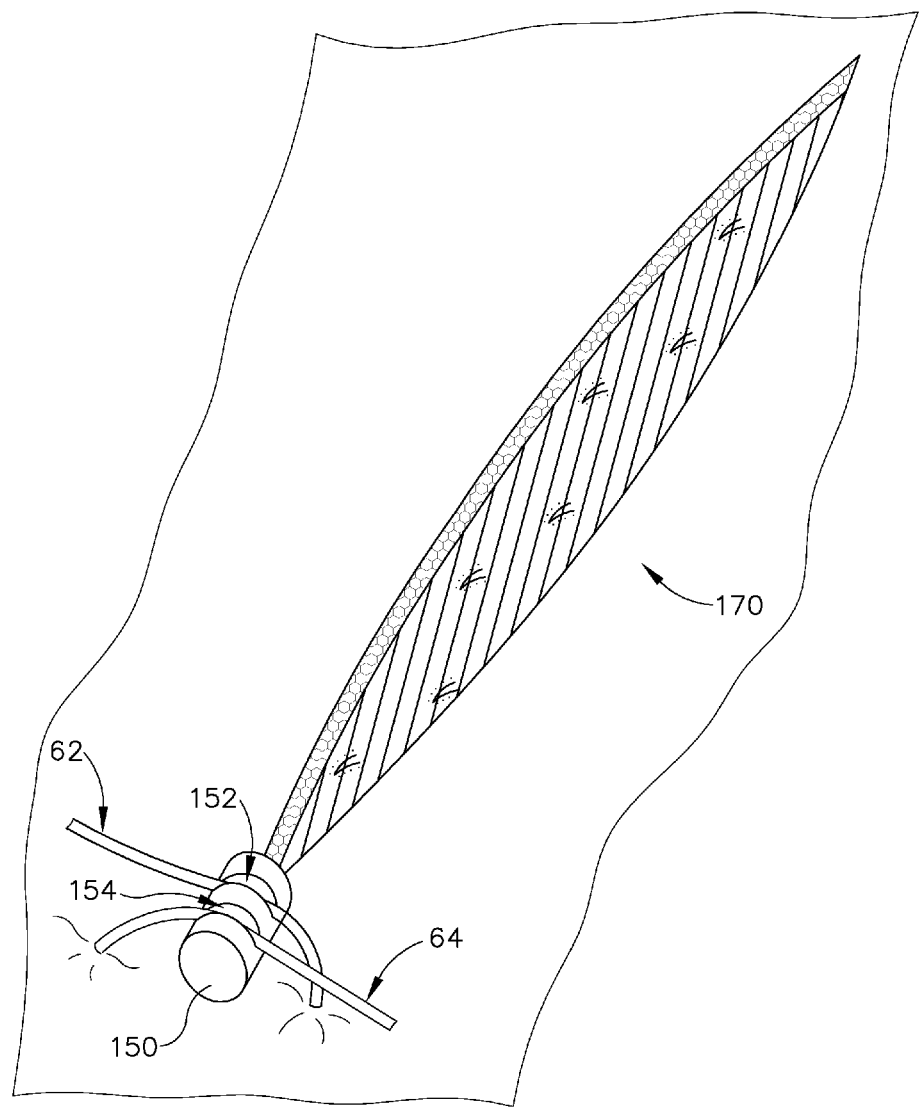
FIG. 7F depicts a perspective view of the suture and incision of FIG. 7A, with the suture fastener securing the severed suture in position to complete a stitch at the incision.
Figure 8:
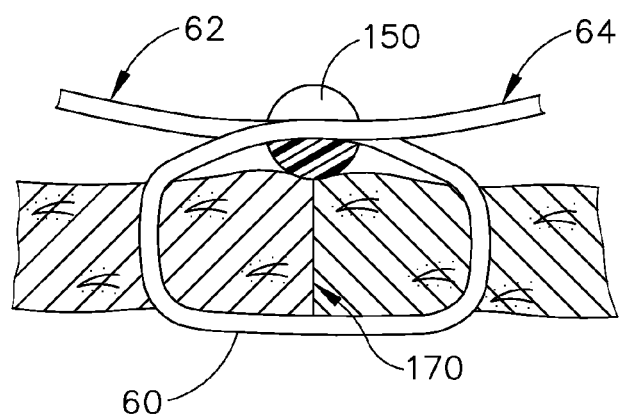
FIG. 8 depicts a side cross-sectional view of the suture, incision, and suture fastener of FIG. 7F.
Figure 9:
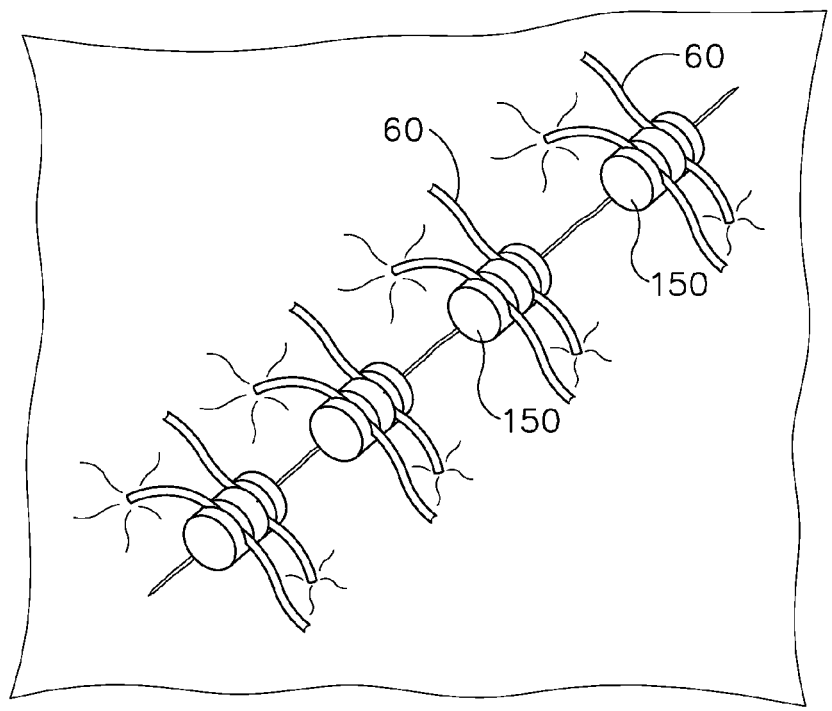
FIG. 9 depicts a series of discrete suture strands and suture fasteners positioned along an incision to create a series of discrete stitches.

FIGS. 7A-7F depict an exemplary use of instrument (100) with suturing instrument (10). As shown in FIG. 7A, suturing instrument (10) is first used to pass needle (50) and suture (60) through tissue adjacent to an incision (170). One strand (62) of suture (60) is positioned in slit (152) of fastener (150). This strand (62) extends from one side of incision (170) and includes a free end of suture (60). Suturing instrument (10) is then pulled away from incision (170) to provide tension in suture (60) as shown in FIG. 7B. Next, suturing instrument (10) is manipulated to wrap suture (60) over shaft (102) as shown in FIG. 7C. Suturing instrument (10) is then manipulated to position another strand (64) of suture (60) in slit (154) of fastener (150) as shown in FIG. 7D, while applying tension to suture (60). This strand (64) extends from the side of incision (170) opposite from the side of incision (170) from which strand (62) extends. It should be understood that the degree of suture (60) tension provided by instrument (10) at this stage will directly affect the degree of tissue approximation at incision (170). Fastener applier (120) is then actuated to lock fastener (150) to both strands (62, 64) simultaneously. With fastener (150) locked to strands (62, 64), end effector (110) is moved to position suture (60) adjacent to jaw (112) while instrument (10) maintains tension in suture (60) as shown in FIG. 7E. Jaw (112) is then clamped onto suture (60) and cutter (114) is actuated to sever suture (60). This leaves secured fastener (150) directly above incision (170), securely holding the remaining suture (60) in place to form a stitch as shown in FIGS. 7F and 8. This process may be repeated with several fasteners (150) to form a series of discrete stitches along incision (170), as shown in FIG. 9, to thereby securely close incision (170) and maintain approximation of tissue at incision (170). Such an arrangement may be referred to as "interrupted suturing." Other suitable ways in which instruments (10, 100) may be used will be apparent to those of ordinary skill in the art in view of the teachings herein.

Figure 10A:
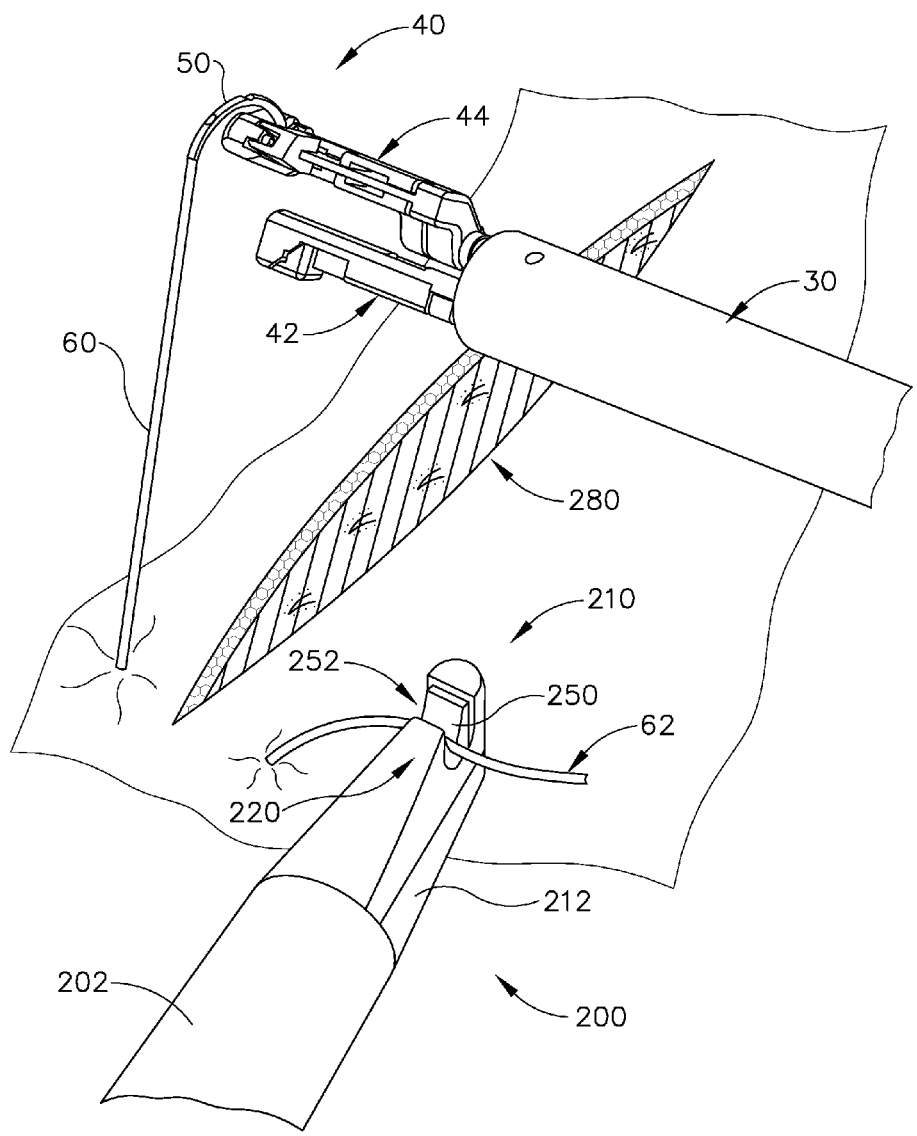
FIG. 10A depicts a perspective view of the suturing instrument of FIG. 1 and another exemplary end effector adjacent to an incision site, with the suturing instrument of FIG. 1 having pulled a suture through tissue and with part of the suture strand received in an exemplary alternative suture fastener of the end effector.

III. Exemplary Suture Fastening and Cutting Instrument with Single Strand Grasping Fasteners FIG. 10A shows another exemplary instrument (200) that is operable to cut a suture (60) and apply fasteners (250) to strands (62, 64) of suture (60). Instrument (200) of this example is substantially similar to instrument (100) described above, and includes a shaft (202) with an end effector (210) at the distal end of shaft. Shaft (202) and end effector (210) of the present example are sized and configured to fit through a conventional trocar for use in a minimally invasive surgical procedure, though it should be understood that shaft (202) and end effector (210) may have any other size and configuration. It should also be understood that numerous kinds of manual and/or automated control features may be provided at the proximal end of shaft (202) to control and drive end effector (210), including but not limited to those mentioned above in the context of instrument (100). Similarly, various kinds of components may be provided within shaft (202) to communicate motion to end effector (210), including but not limited to those mentioned above in the context of instrument (100). Various kinds of suitable components and features that may be provided within shaft (202) and at the proximal end of shaft (202) to operate end effector (210) will be apparent to those of ordinary skill in the art in view of the teachings herein.

End effector (210) of the present example includes a pivoting jaw (212) and a fastener applier (220). Pivoting jaw (212) is operable to pivot toward and away from fastener applier (220), in a manner similar to that described above with respect to jaw (112). Similarly, end effector (210) includes a translating cutter (not shown) that is operable similar to cutter (114) described above. Fastener applier (220) is configured to receive and actuate a fastener (250). Fastener (250) of the present example comprises a single slit (252). It should be understood that fastener (250) may be otherwise configured and operable in accordance with the above teachings relating to fastener (150). In other words, the only difference between fastener (250) of this example and fastener (150) of the previous example is that fastener (250) has just a single slit (252) while fastener (150) has a pair of slits (152, 154). It should also be understood that end effector (210) may be configured to hold just a single fastener (250) at a time (e.g., with additional fasteners (250) being held on something similar to sheath (160) described above, etc.); or end effector (210) may hold several fasteners (250) in an end-to-end configuration or otherwise. Other suitable features and configurations for fastener applier (220) and fasteners (250) will be apparent to those of ordinary skill in the art in view of the teachings herein.

Figure 10B:
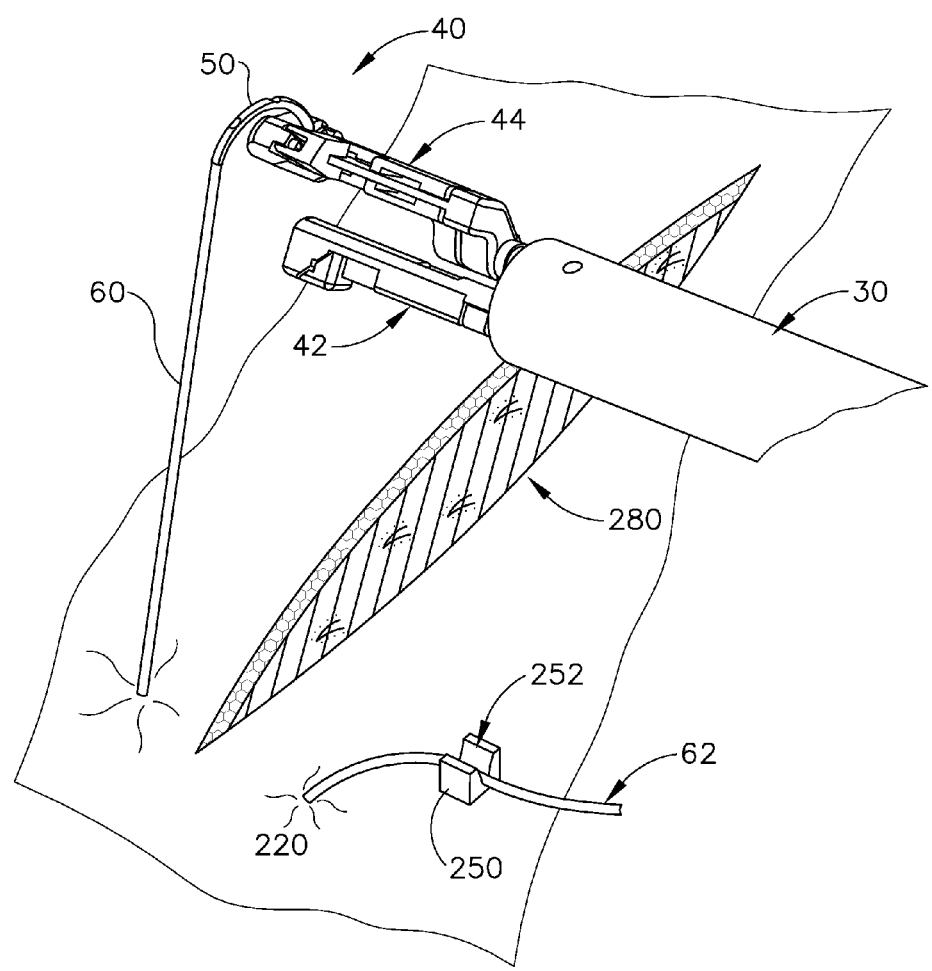
FIG. 10B depicts a perspective view of the suturing instrument of FIG. 1 and the suture with the suture fastener of FIG. 10A secured to the suture.
Figure 10C:
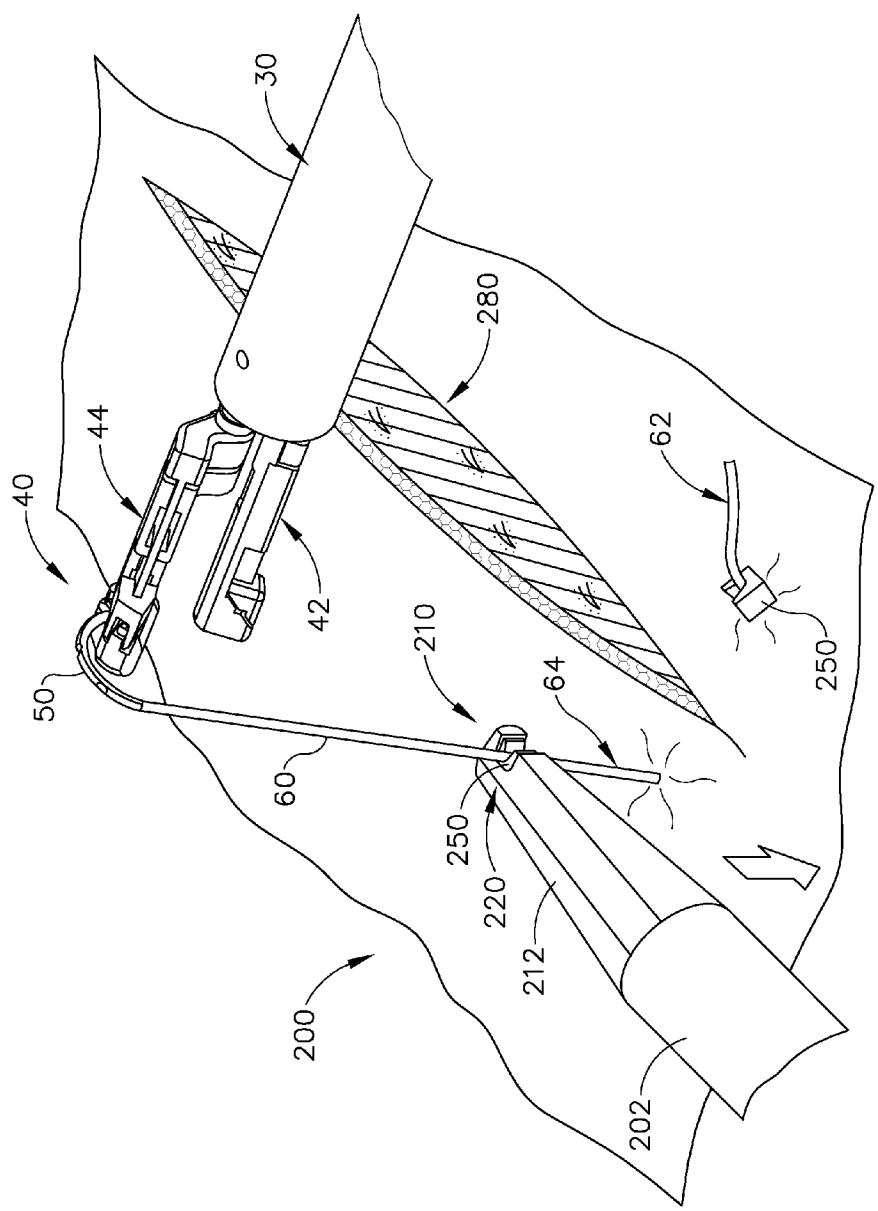
FIG. 10C depicts a perspective view of the suturing instrument of FIG. 1 and the end effector of FIG. 10A positioned to secure another suture fastener to the suture.
Figure 10D:
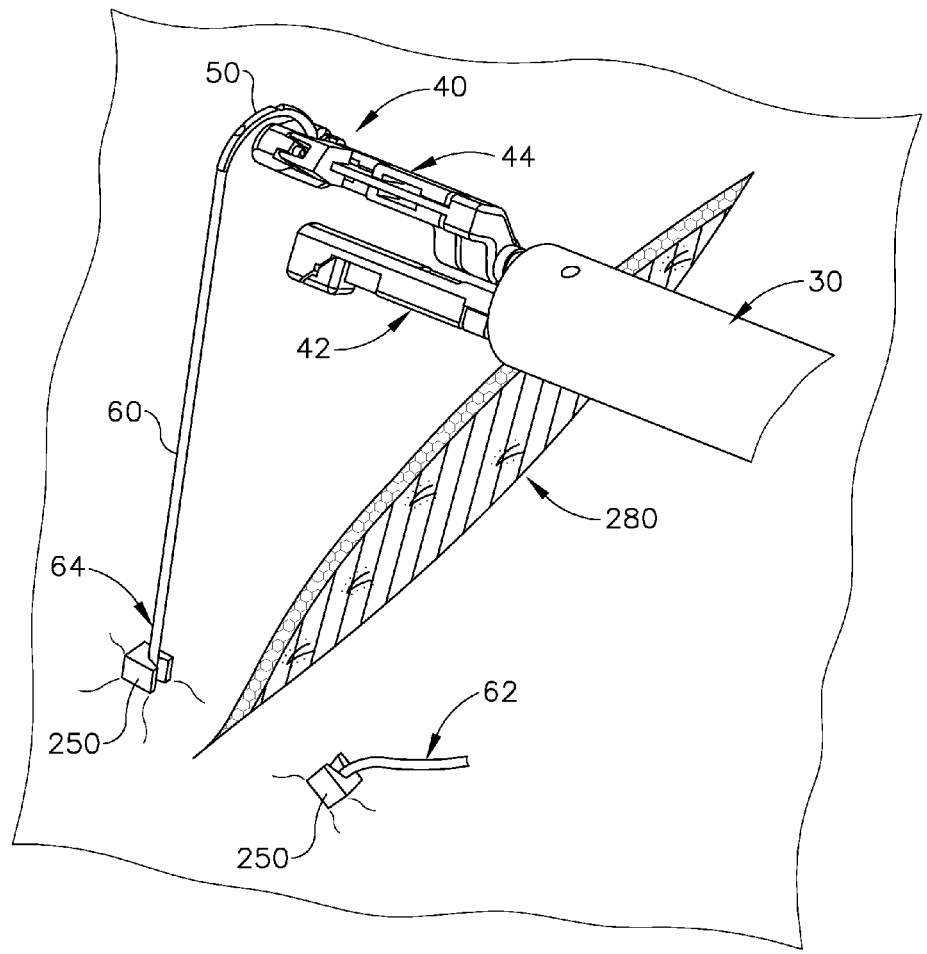
FIG. 10D depicts a perspective view of the suturing instrument of FIG. 1 and the suture with the suture fastener of FIG. 10A and the suture fastener of FIG. 10C both secured to the suture on opposite sides of the incision.

FIGS. 10A-10F depict an exemplary use of instrument (200) with suturing instrument (10). As shown in FIG. 10A, suturing instrument (10) is first used to pass needle (50) and suture (60) through tissue adjacent to an incision (270). One strand (62) of suture (60) is positioned in slit (252) of fastener (250). This strand (62) extends from one side of incision (170) and includes a free end of suture (60). Fastener applier (220) is then actuated to lock fastener (250) to strand (62) of suture (60), as shown in FIG. 10B. Suturing instrument (10) is then pulled away from incision (270) to provide tension in suture (60), as end effector (210) is repositioned with another fastener (250), to position another strand (64) of suture (60) in slit (252) of this other fastener (250) as shown in FIG. 10C. This strand (64) extends from the side of incision (270) opposite from the side of incision (270) from which strand (62) extends. End effector (210) is slid down the length of strand (64) until end effector (210) contacts tissue adjacent to incision (270), and fastener applier (220) is then actuated to lock fastener (250) to strand (64) of suture (60) while instrument (10) holds suture (60) in tension, resulting in the configuration shown in FIG. 10D. It should thus be understood that this example provides fasteners (250) on both sides of incision (270). It should also be understood that the length of suture (60) extending underneath incision (270) and between fasteners (250) remains under some degree of tension; and that fasteners (250) are sized to remain against tissue without being pulled through the tissue, such that fasteners (250) serve as anchors for suture (60) to maintain approximation of tissue at incision (270). By way of example only, end effector (210) may be pressed against the tissue during the transition between the stages shown in FIGS. 10C and 10D, to provide a desired amount of tension in the length of suture (60) extending under incision (270) between fasteners (250).

Figure 10E:
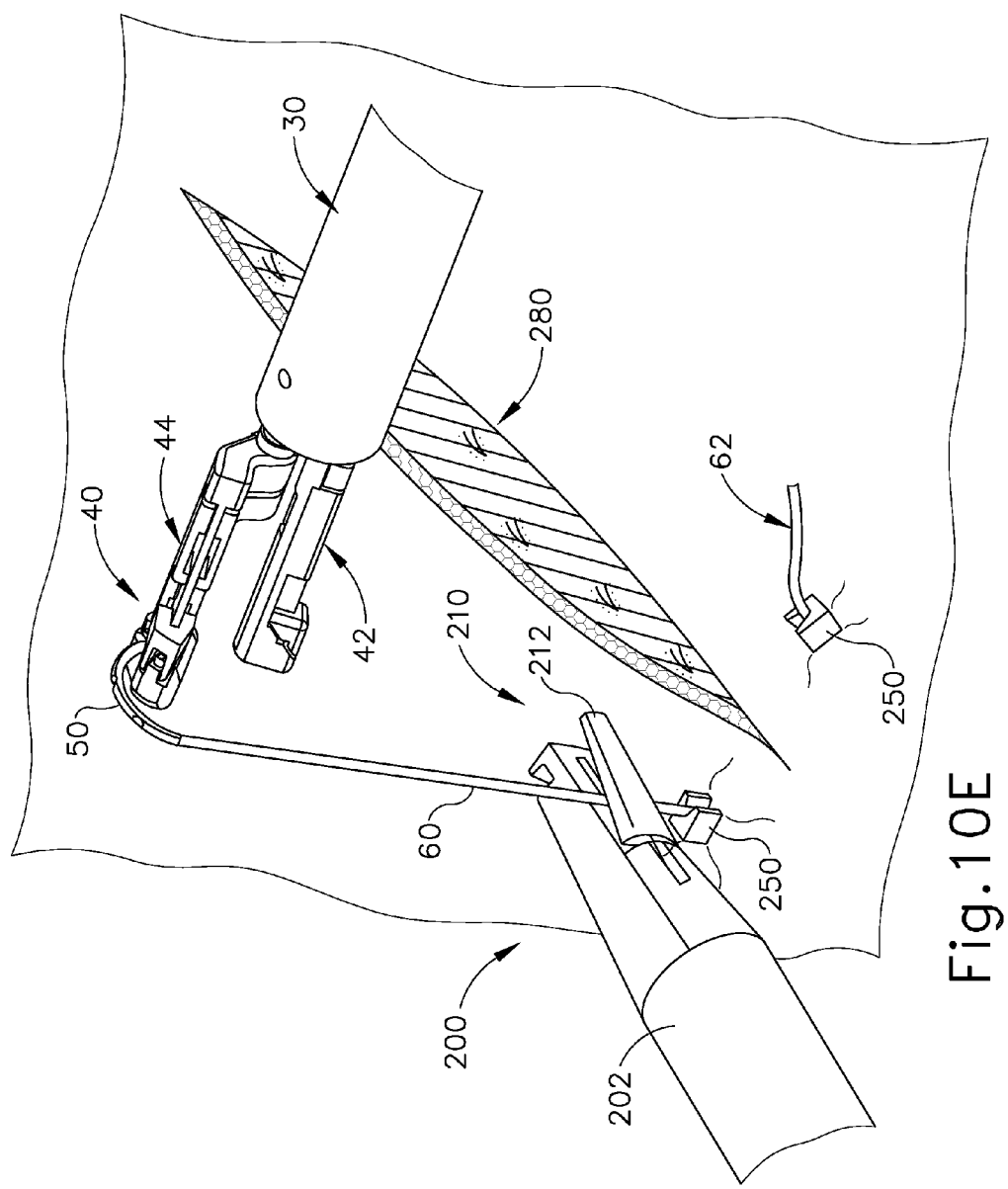
FIG. 10E depicts a perspective view of the suturing instrument of FIG. 1 and the end effector of FIG. 10A positioned to sever the suture while the suturing instrument of FIG. 1 holds the suture in tension.
Figure 10F:
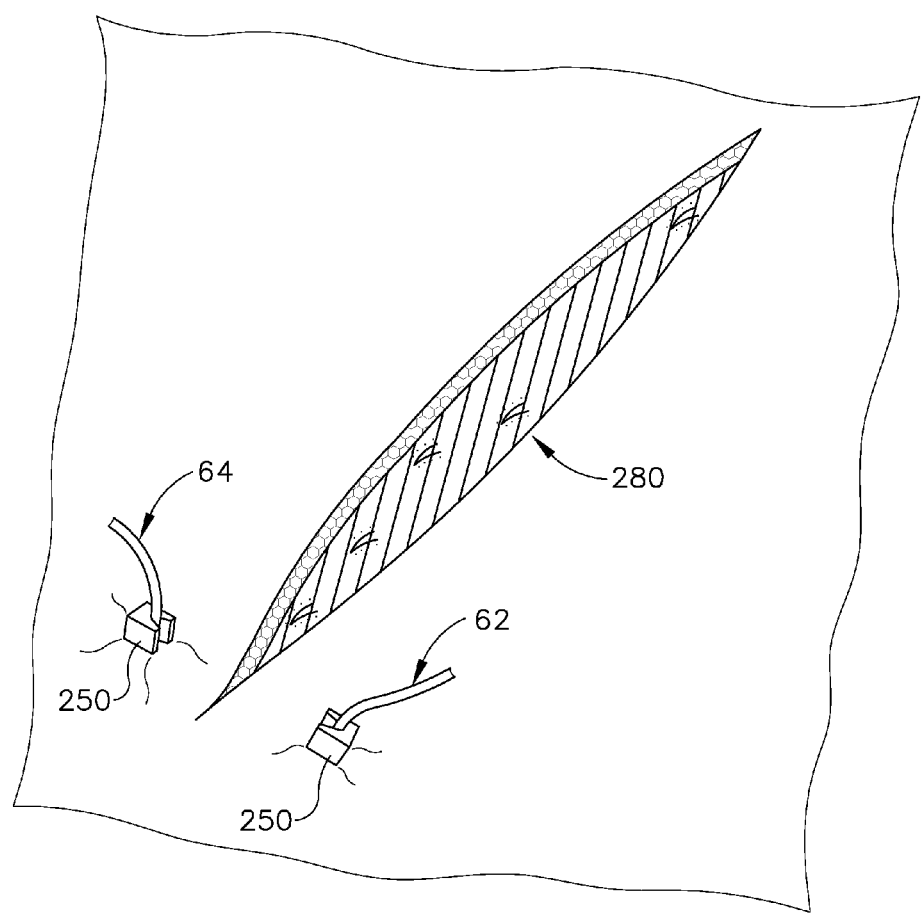
FIG. 10F depicts a perspective view of the suture and incision of FIG. 10A with the suture fastener of FIG. 10A and the suture fastener of FIG. 10C in place to complete a stitch at the incision.
Figure 11:
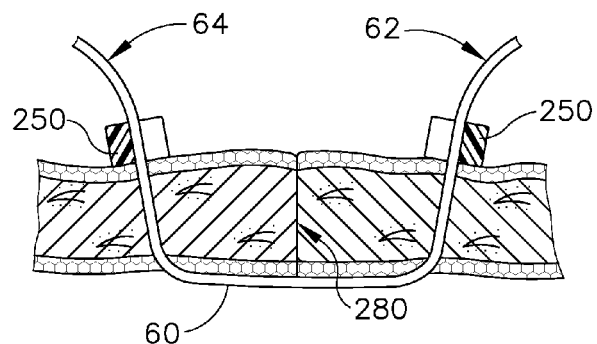
FIG. 11 depicts a side cross-sectional view of the suture, incision, and suture fasteners of FIG. 10F.
Figure 12:
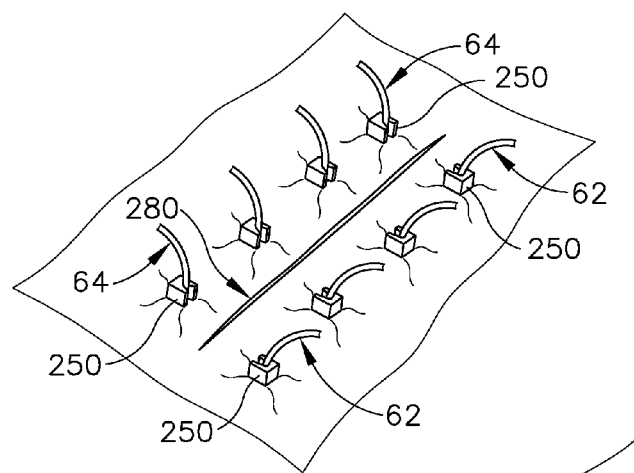
FIG. 12 depicts a series of discrete suture strands and suture fasteners positioned along an incision to create a series of discrete stitches.
Figure 13:
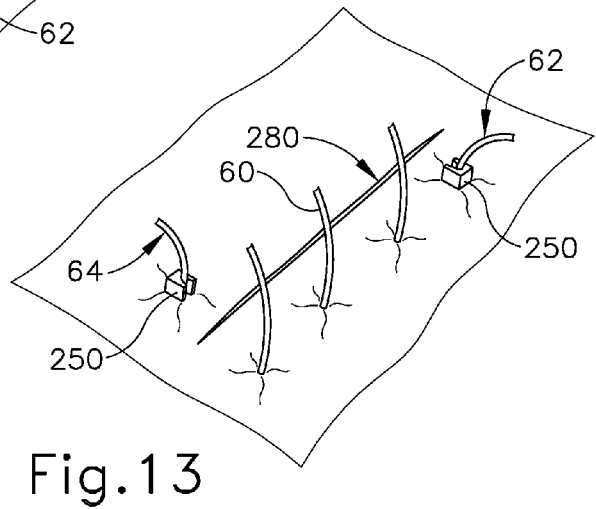
FIG. 13 depicts a single suture strand creating a series of stitches at an incision and a pair of suture fasteners at each end of the suture to secure the stitches in place.

With both fasteners (250) secured in place, end effector (210) is positioned to place suture (60) adjacent to jaw (212) while instrument (10) maintains tension in suture (60) as shown in FIG. 10E. Jaw (212) is then clamped onto suture (60) and the cutter is actuated to sever suture (60). This leaves secured fasteners (250) on opposite sides of incision (270), securely holding the remaining suture (60) in place to form a stitch as shown in FIGS. 10F and 11. This process may be repeated with several pairs of fastener (250) to form a series of discrete stitches along incision (270), as shown in FIG. 12, to thereby securely close incision (270). Such an arrangement may be referred to as "interrupted suturing." As another merely illustrative variation shown in FIG. 13, a first fastener (250) may be secured at one end of incision (270), then instrument (10) may be used to weave needle (50) and suture (60) through tissue to form several stitches over incision (270), then a second fastener (250) may be secured to the other end of incision (270) to secure suture (60) in place. Such an arrangement may be referred to as "continuous suturing." Other suitable ways in which instruments (10, 200) may be used will be apparent to those of ordinary skill in the art in view of the teachings herein. By way of example only, in some versions a fastener (250) is pre-applied to one end of suture (60) before instrument is used to drive needle (50) and suture (60) through tissue to reach the configuration shown in FIG. 10B.

IV. Exemplary Suture Fastening and Cutting Instrument with Fastener Applier and Suture Cutter in Jaws FIGS. 14A-14I show another exemplary instrument (300) that is operable to cut a suture (60) and apply fasteners (350) to strands (62, 64) of suture (60). Instrument (300) of this example includes a shaft (302) with an end effector (310) at the distal end of shaft. Shaft (302) and end effector (310) of the present example are sized and configured to fit through a conventional trocar for use in a minimally invasive surgical procedure, though it should be understood that shaft (302) and end effector (310) may have any other size and configuration. It should also be understood that numerous kinds of manual and/or automated control features may be provided at the proximal end of shaft (302) to control and drive end effector (310), including but not limited to those mentioned above in the context of instrument (100). Similarly, various kinds of components may be provided within shaft (302) to communicate motion to end effector (310), including but not limited to those mentioned above in the context of instrument (100). Various kinds of suitable components and features that may be provided within shaft (302) and at the proximal end of shaft (302) to operate end effector (310) will be apparent to those of ordinary skill in the art in view of the teachings herein.

End effector (310) of the present example includes a pivoting jaw (312) and a fastener applier (320) located within an interior region of a fixed jaw (314). Pivoting jaw (312) is operable to pivot toward and away from fixed jaw (314), in a manner similar to that described above with respect to jaw (112). Similarly, end effector (310) includes a translating cutter (not shown) that is operable similar to cutter (114)

described above. Fastener applier (320) is configured to receive and actuate a fastener (350). Fastener (350) of the present example comprises features operable to selectively grip two strands (62, 64) of suture (60) in two stages, as will be described in greater detail below. Fastener (350) may be configured in accordance with the various teachings herein, and it should be understood that various other types of fasteners may be used with fastener applier (320). Similarly, other suitable ways in which fastener (350) may be configured will be apparent to those of ordinary skill in the art in view of the teachings herein. It should also be understood that end effector (310) may be configured to hold just a single fastener (350) at a time (e.g., with additional fasteners (350) being held on something similar to sheath (160) described above, etc.); or end effector (310) may hold several fasteners (350) in an end-to-end configuration or otherwise. Other suitable features and configurations for fastener applier (320) will be apparent to those of ordinary skill in the art in view of the teachings herein.

Figure 14A:
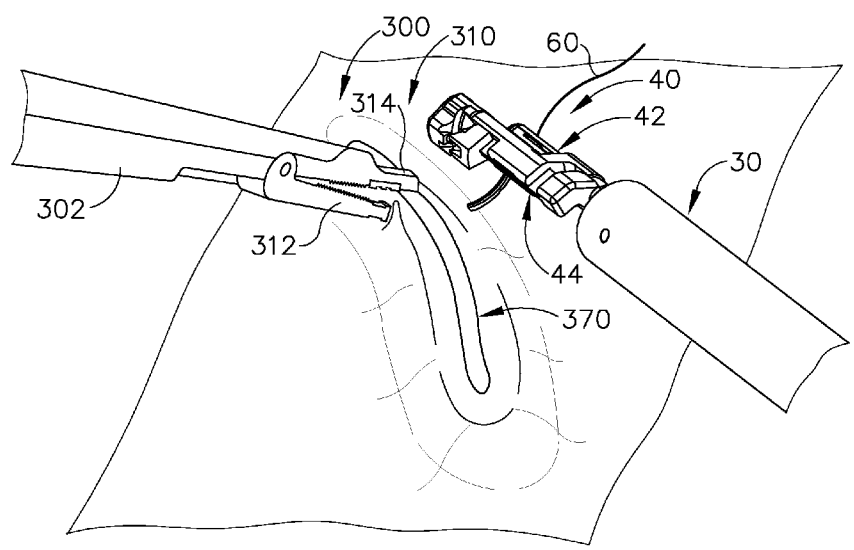
FIG. 14A depicts a perspective view of the suturing instrument of FIG. 1 and another exemplary end effector adjacent to an incision site, with the end effector grasping tissue at one side of the incision as the suturing instrument approaches the incision with a needle and suture.
Figure 14B:
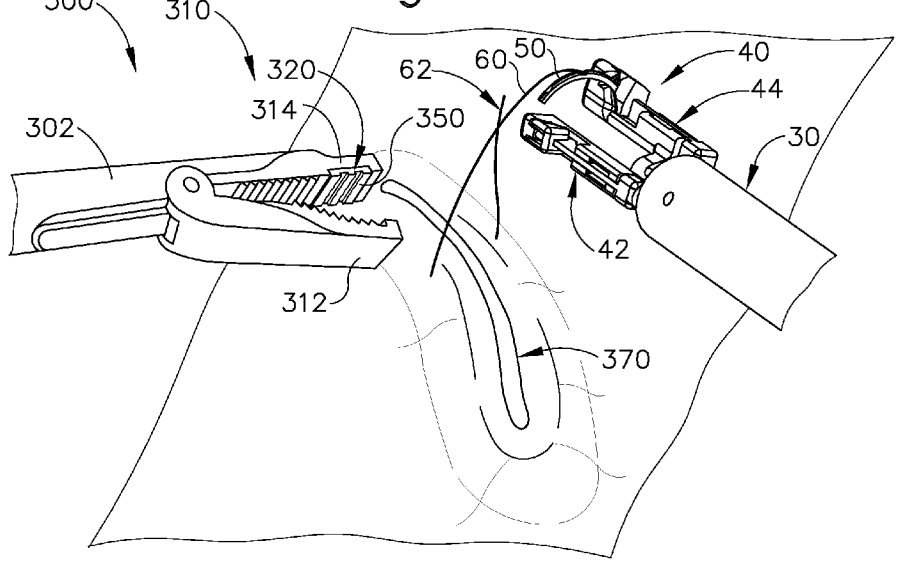
FIG. 14B depicts a perspective view of the suturing instrument of FIG. 1 and the end effector of FIG. 14A, with the suturing instrument having pulled the suture through tissue.
Figure 14C:
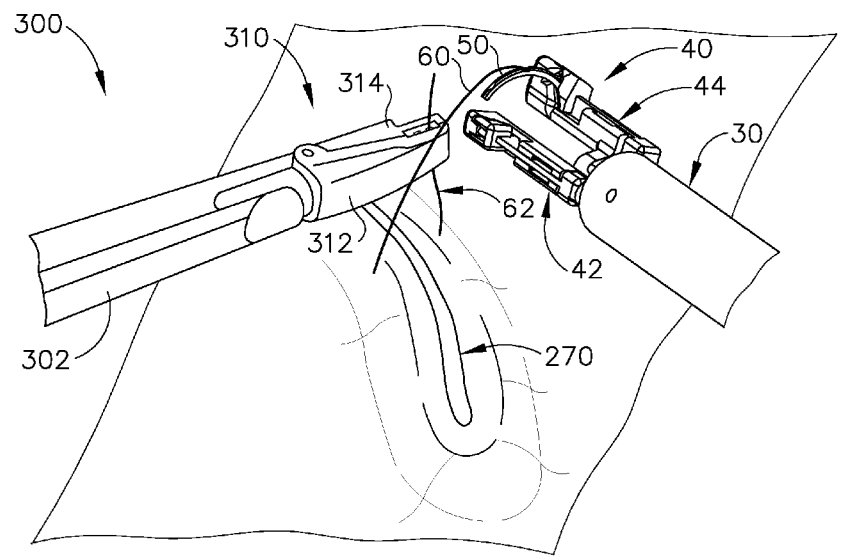
FIG. 14C depicts a perspective view of the suturing instrument of FIG. 1 and the end effector of FIG. 14A, with the jaw of the end effector closed about a first strand portion of the suture to secure an exemplary alternative suture fastener to the first strand portion.
Figure 14D:
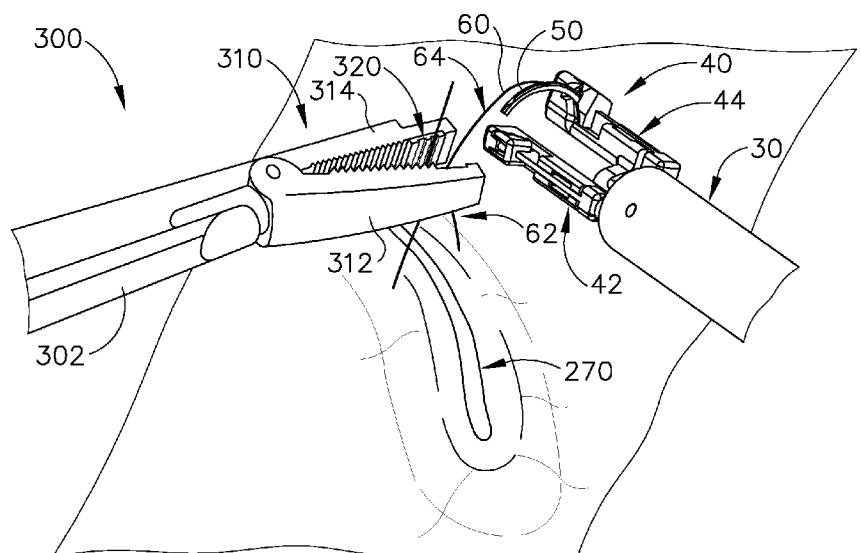
FIG. 14D depicts a perspective view of the suturing instrument of FIG. 1 and the end effector of FIG. 14A, with the jaw of the end effector opened to receive a second strand portion of the suture.
Figure 14E:
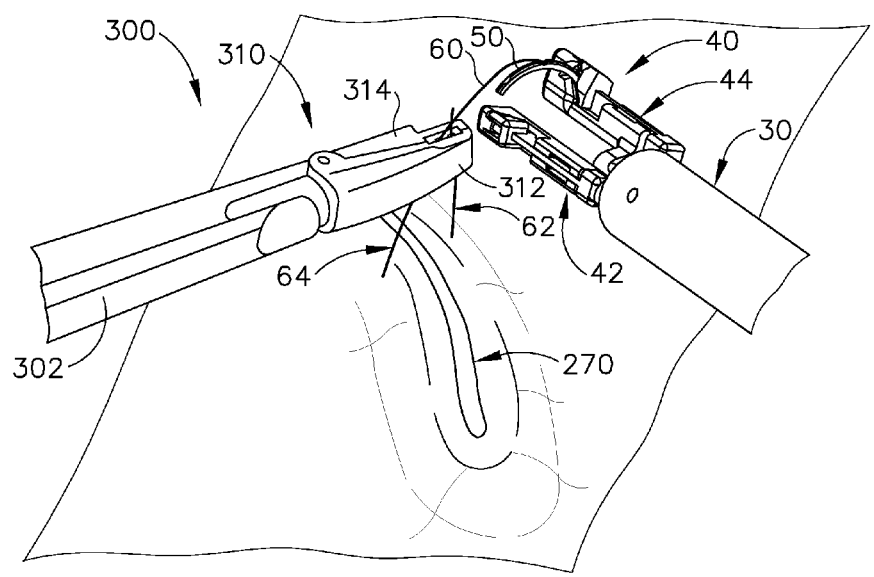
FIG. 14E depicts a perspective view of the suturing instrument of FIG. 1 and the end effector of FIG. 14A, with the jaw of the end effector closed about the second strand portion before securing the suture fastener to the second strand portion.
Figure 14F:
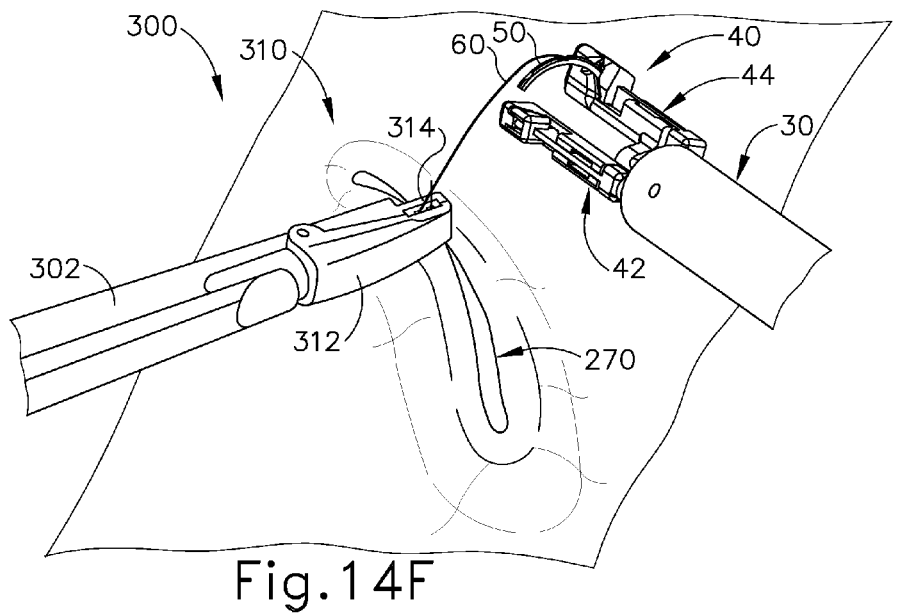
FIG. 14F depicts a perspective view of the suturing instrument of FIG. 1 and the end effector of FIG. 14A, with the suturing instrument applying tension to the suture while the end effector secures the suture fastener to the second strand portion.

FIGS. 14A-14I depict an exemplary use of instrument (300) with suturing instrument (10). As shown in FIG. 10A, suturing instrument (10) approaches an incision (370) while end effector (310) grasps tissue on one side of incision (370) with jaws (312, 314). Instrument (10) is then used to pass needle (50) and suture (60) through the tissue adjacent to incision (370) as shown in FIG. 14B. At this stage, a strand (62) extends from one side of incision (370) and includes a free end of suture (60). End effector (310) is then positioned to grasp strand (62) between jaws (312, 314) as shown in FIG. 14C. While strand (62) is grasped between jaws (312, 314), fastener applier (320) is partially actuated to secure fastener (350) to strand (62). Various suitable ways in which such actuation may be provided will be apparent to those of ordinary skill in the art in view of the teachings herein. Jaws (312, 314) are then opened as shown in FIG. 14D, with fastener (350) remaining disposed in fixed jaw (314). End effector (310) is then repositioned to grasp another strand (64) of suture (600 between jaws (312, 314) as shown in FIG. 14E. This strand (64) extends from the side of incision (370) opposite from the side of incision (370) from which strand (62) extends. End effector (310) is slid down the length of strand (64) until end effector (310) contacts tissue adjacent to incision (370), while instrument (10) holds suture (60) in tension as shown in FIG. 14F. This combination of end effector (310) pressing against the tissue and instrument (10) pulling on suture (60) may provide a desired amount of tension in the length of suture (60) extending under incision (370).

Figure 14G:
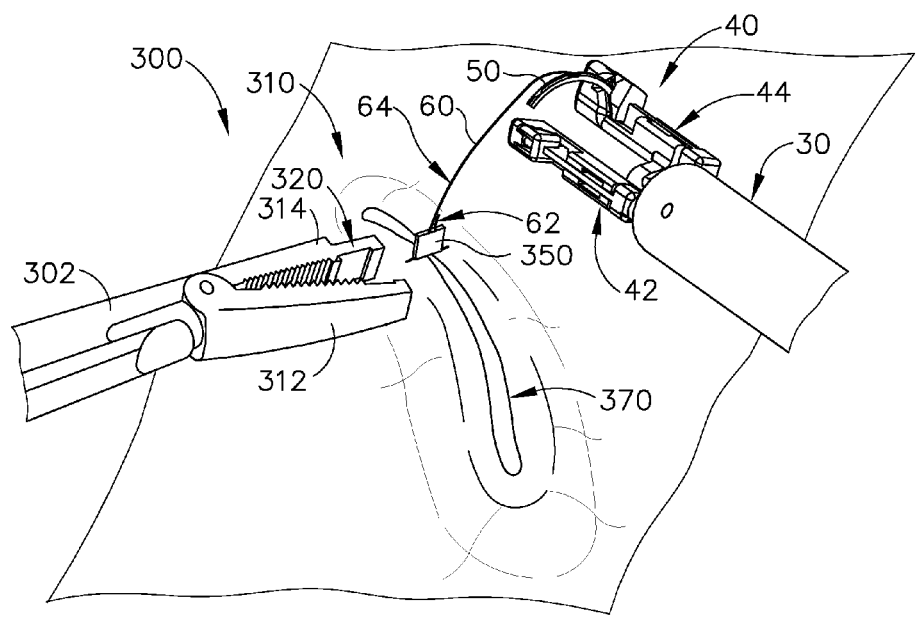
FIG. 14G depicts a perspective view of the suturing instrument of FIG. 1 and the end effector of FIG. 14A, with the jaw of the end effector open to release the suture fastener, and with the suture fastener secured to the first and second strand portions of the suture.
Figure 14H:
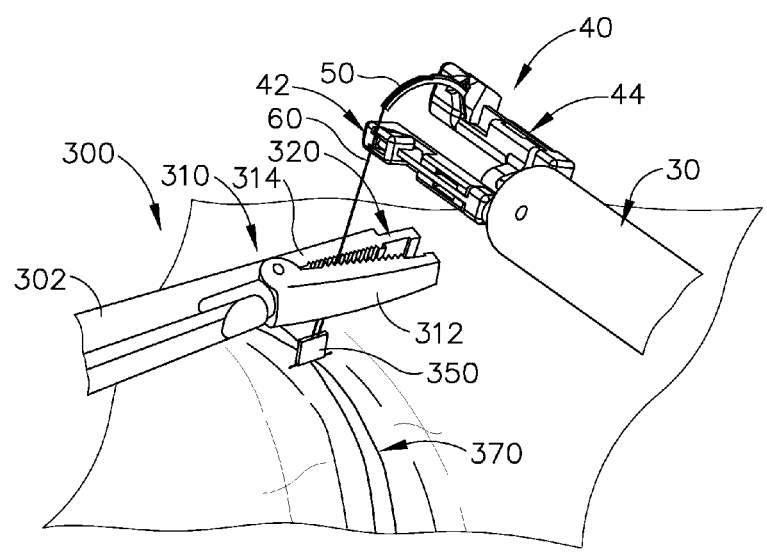
FIG. 14H depicts a perspective view of the suturing instrument of FIG. 1 and the end effector of FIG. 14A, with the suturing instrument applying tension to the suture while the end effector severs the suture.
Figure 14I:
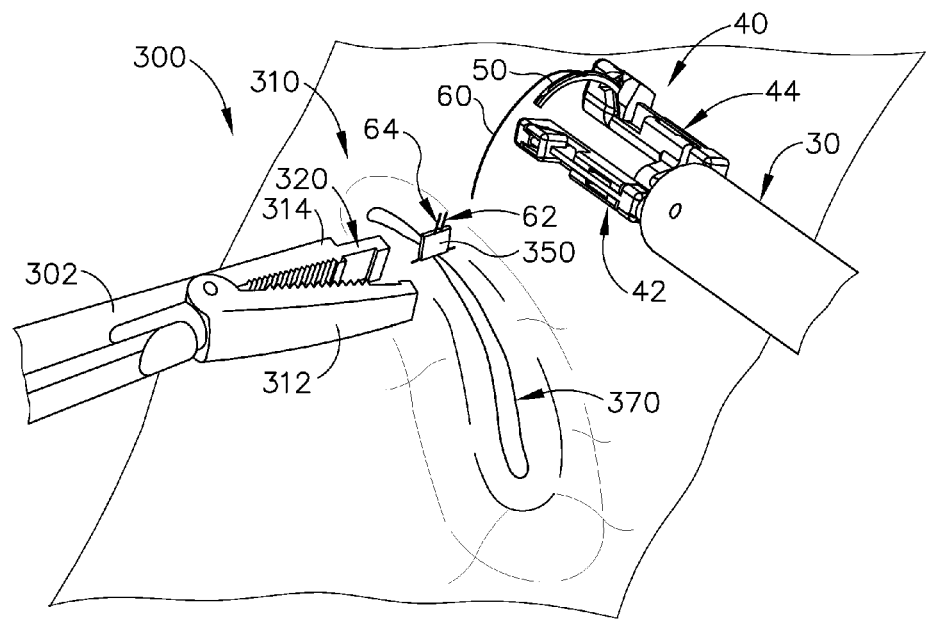
FIG. 14I depicts a perspective view of the suture and incision of FIG. 14A with the suture fastener secured in place to complete a stitch at the incision.

With the desired amount of tension provided in suture (60), fastener applier (320) is then actuated to lock fastener (350) to strand (64), and fastener (350) is then released from fastener applier (320). Various suitable ways in which fastener (350) may be released from fastener applier (320) will be apparent to those of ordinary skill in the art in view of the teachings herein. Jaws (312, 314) are then opened and end effector (310) is pulled away from fastener (350) as shown in FIG. 14G. Next, end effector (310) is positioned to place strand (60) in an apex region between jaws (312, 314) associated with a suture cutter as shown in FIG. 14H. The suture cutter is actuated to sever suture (60), then end effector (310) is again pulled away as shown in FIG. 14I. This leaves secured fastener (350) directly above incision (370), securely holding the remaining suture (60) in place to form a stitch. This process may be repeated with several fasteners (350) to form a series of discrete stitches along incision (370), to thereby securely close incision (370) and maintain approximation of tissue at incision (370) through "interrupted suturing." Other suitable ways in which instruments (10, 300) may be used will be apparent to those of ordinary skill in the art in view of the teachings herein.

Figure 15:
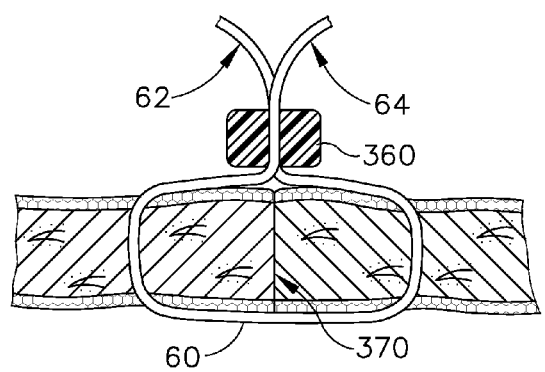
FIG. 15 depicts a side cross-sectional view of a suture, incision, and exemplary alternative suture fastener.
Figure 16:
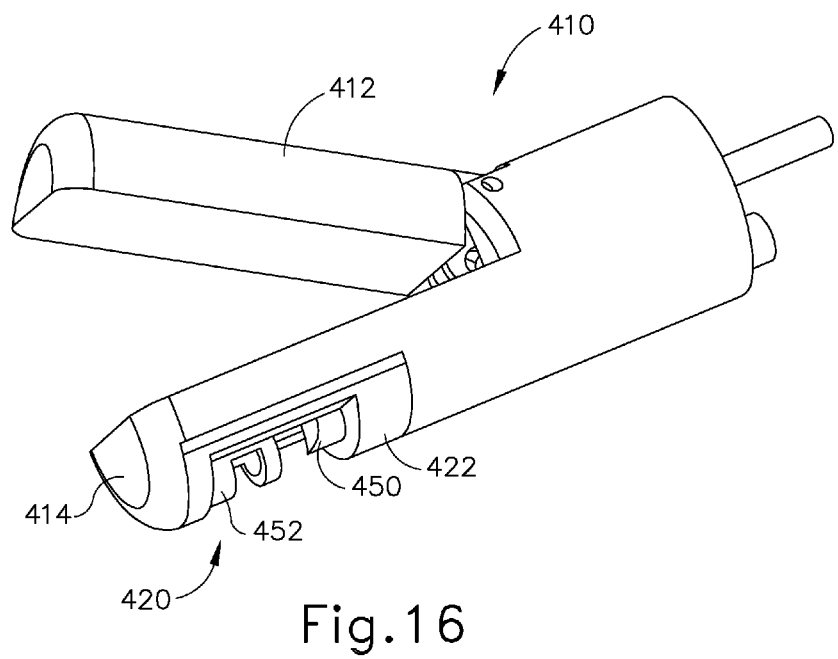
FIG. 16 depicts a perspective view of an exemplary alternative end effector with a suture fastening cartridge.

In the example depicted in FIGS. 14A-14I, strands (62, 64) that are secured by fastener (350) are positioned along a plane that is substantially transverse to incision (370). In some other versions, secured strands (62, 64) are positioned along a plane that is substantially parallel to incision (370). By way of example only, FIG. 15 shows an exemplary fastener (360) that secures strands (62, 64) in a position where strands (62, 64) lie along a plane that is substantially parallel to incision (370). Some versions of fastener applier (320) may be configured to readily accommodate such a fastener (360). Other suitable types of fastener appliers that may accommodate fastener (360) will be apparent to those of ordinary skill in the art in view of the teachings herein. Similarly, other suitable types of fasteners that may be used with fastener applier (320) will be apparent to those of ordinary skill in the art in view of the teachings herein.

V. Exemplary Suture Fastening and Cutting Instrument with Fastener Cartridge

FIGS. 16-18C show another exemplary end effector (410) that is operable to apply a fastener (450, 452) to strands (62, 64) of suture (60). End effector (410) is positioned at the distal end of a shaft (not shown). The shaft and end effector (410) of the present example are sized and configured to fit through a conventional trocar for use in a minimally invasive surgical procedure, though it should be understood that the shaft and end effector (410) may have any other size and configuration. It should also be understood that numerous kinds of manual and/or automated control features may be provided at the proximal end of the shaft to control and drive end effector (410), including but not limited to those mentioned above in the context of instrument (100). Similarly, various kinds of components may be provided within the shaft to communicate motion to end effector (410), including but not limited to those mentioned above in the context of instrument (100). Various kinds of suitable components and features that may be provided within the shaft and at the proximal end of the shaft to operate end effector (410) will be apparent to those of ordinary skill in the art in view of the teachings herein.

Figure 17:
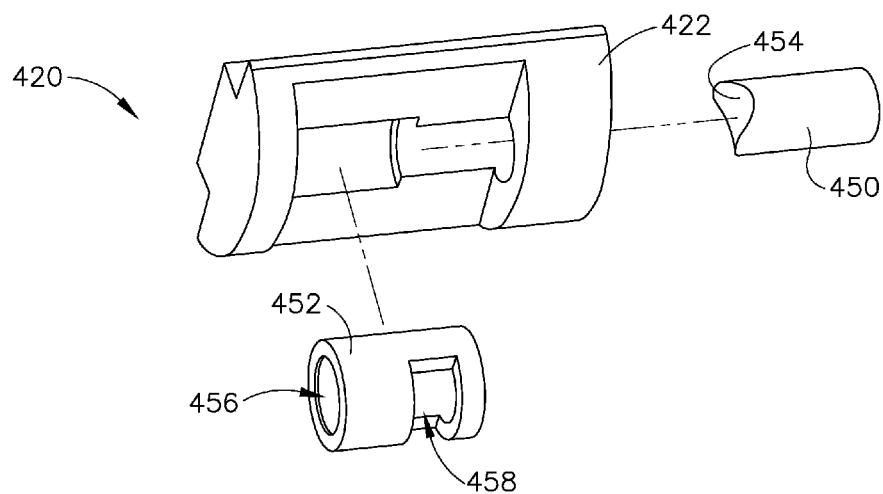
FIG. 17 depicts an exploded perspective view of the suture fastening cartridge of FIG. 16.

End effector (410) of the present example includes a pivoting jaw (412) and a fastener cartridge (420) located on an exterior region of a fixed jaw (414). Pivoting jaw (412) is operable to pivot toward and away from fixed jaw (414), in a manner similar to that described above with respect to jaw (112). Similarly, end effector (410) includes a translating cutter (not shown) that is operable similar to cutter (114) described above. Of course, as with any other pivotable jaw and cutter mentioned herein, jaw (412) and/or the cutter may be omitted if desired. Fastener cartridge (420) is removably received in fixed jaw (414), such that fastener cartridge (420) may be readily replaced while end effector (410) is disposed within a patient. In other words, fixed jaw (414) may be reloaded repeatedly with different fastener cartridges (420) without having to extract end effector (410) from the patient (e.g., via a trocar). As best seen in FIG. 17, fastener cartridge (420) of this example includes a cartridge body (422) that receives an inner fastener member (450) and an outer fastener member (452), which cooperate together to form a fastener as will be described in greater detail below. Inner fastener member (450) includes a contoured distal face (454); while outer fastener member (452) defines a bore (456) and a lateral aperture (458).

Figure 18A:
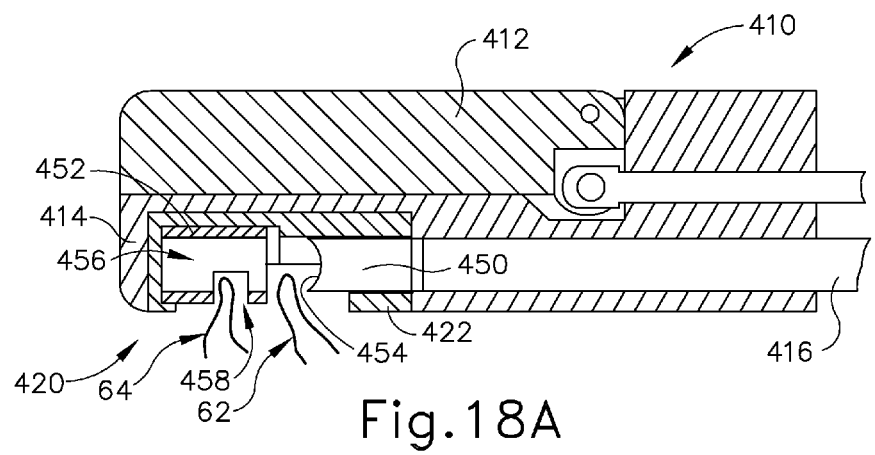
FIG. 18A depicts a side cross-sectional view of the end effector of FIG. 16 with an inner fastener member in a proximal position, with a first suture strand positioned in a gap between the inner fastener member and an outer fastener member, and with a second suture strand positioned in a notch of the outer fastener member.
Figure 18B:
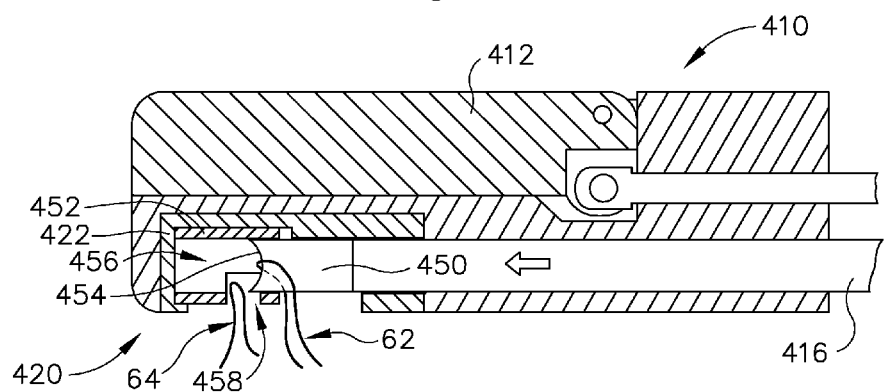
FIG. 18B depicts a side cross-sectional view of the end effector of FIG. 16 with the inner fastener member advanced distally to an intermediate position within the outer fastener member to capture the first suture strand between the inner fastener member and the outer fastener member.
Figure 18C:
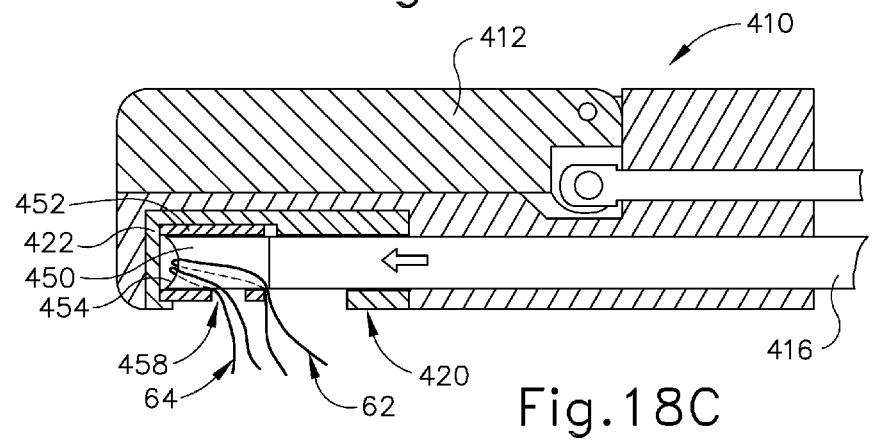
FIG. 18C depicts a side cross-sectional view of the end effector of FIG. 16 with the inner fastener member advanced distally to a fully actuated position within the outer fastener member to capture both the first and second suture strands between the inner fastener member and the outer fastener member.

FIGS. 18A-18C depict an exemplary use of end effector (410). It should be understood that end effector (410) may be used in cooperation with suturing instrument (10) at an incision in accordance with the various teachings herein, to secure a suture (60) relative to the incision to thereby provide one or more secure stitches at the incision. As shown in FIG. 18A, inner fastener member (450) is in a proximal position spaced apart from outer fastener member (452). One strand (62) of suture (60) is positioned in the gap defined between inner fastener member (450) and outer fastener member (452). Another strand (64) of suture (60) is positioned in lateral aperture (458) of outer fastener member (452), though it should be understood that in some versions strand (64) is not positioned in lateral aperture (458) until a later stage in the process. Next, a push rod (416) is actuated distally to push inner fastener member (450) into bore (456) of outer fastener member (452) as shown in FIG. 18B. The contour of distal face (454) ensures that strand (62) remains in contact with distal face (454) during this distal advancement of inner fastener member (450). It should also be understood that strand (62) is captured between the outer diameter of inner fastener member (450) and the inner diameter of outer fastener member (452) at this stage.

To the extent that strand (64) has not already been positioned in lateral aperture (458) of outer fastener member (452), strand (64) is now positioned in lateral aperture (458) of outer fastener member (452). Push rod (416) is then actuated further distally to push inner fastener member (450) further into bore (456) of outer fastener member (452) as shown in FIG. 18C. The contour of distal face (454) ensures that strand (64) is now also in contact with distal face (454) in addition to strand (62) being in contact with distal face. With inner fastener member (450) being advanced to the distal position shown in FIG. 18C, both strands (62, 64) are now captured between the outer diameter of inner fastener member (450) and the inner diameter of outer fastener member (452). Furthermore, fastener members (450, 452) are configured to provide a press fit or snap fit once inner fastener member (450) reaches this distal position, thereby substantially securing fastener members (450, 452) together. In some versions, the outer edge of distal face (454) is slightly rounded or chamfered to avoid inadvertent shearing of strands (62, 64) as inner fastener member (450) is advanced to the distal-most position within outer fastener member (452).

At this stage, the inner diameter of outer fastener member (452) and the outer diameter of inner fastener member (450) cooperate to provide sufficient friction to substantially secure both strands (62, 64) relative to fastener members (450, 452). End effector (410) then ejects or otherwise releases the assembly of fastener members (450, 452) and strands (62, 64) from cartridge body (422). For instance, a ramp or other type of camming feature may be configured to eject or otherwise release fastener members (450, 452) from cartridge body (422) as soon as push rod (416) reaches a distal position. Various suitable components, features, and configurations that may be used to provide ejection or release of release fastener members (450, 452) from cartridge body (422) will be apparent to those of ordinary skill in the art in view of the teachings herein. With the assembly of fastener members (450, 452) and strands (62, 64) released from cartridge body (422), the cooperating fastener members (450, 452) secure suture (60) relative to an incision just like any other fastener described herein, thereby securing one or more stitches at the incision. Of course, cartridge (420) may be replaced any desired number of times, to apply any desired number of additional fasteners (450, 452) to suture (60) to provide one or more additional stitches at the incision site.

Figure 19:
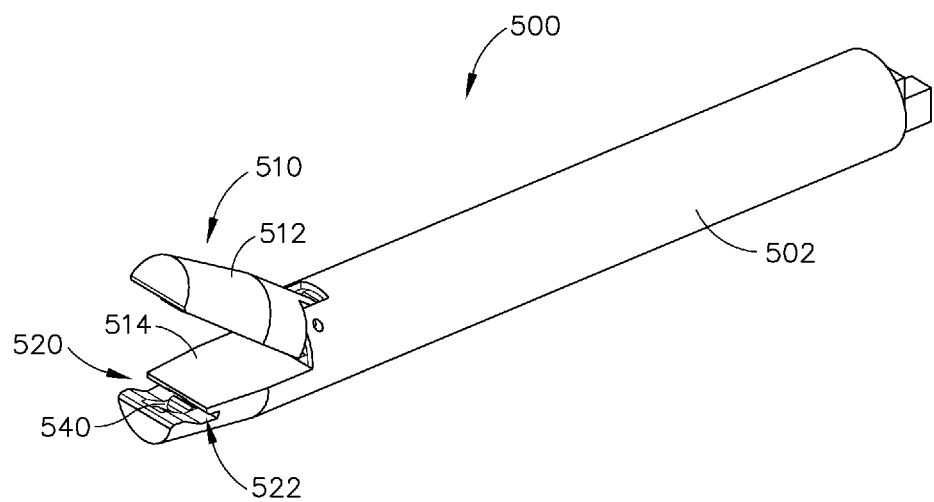
FIG. 19 depicts another exemplary alternative end effector.
Figure 20A:
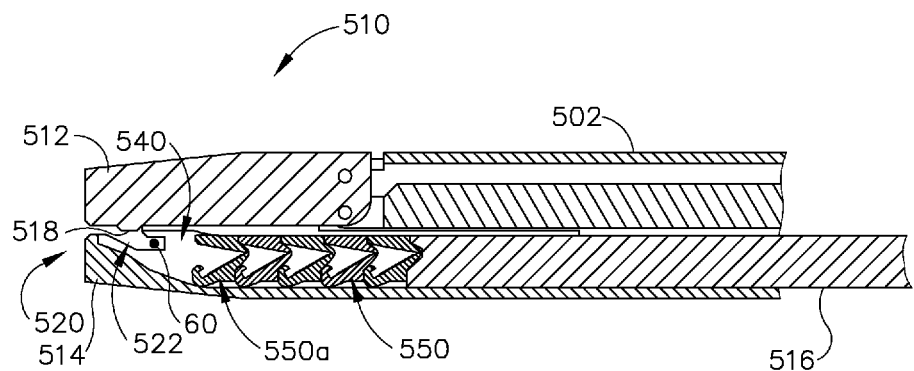
FIG. 20A depicts a side cross-sectional view of the end effector of FIG. 19 with a plurality of fasteners arranged in an end-to-end configuration, and with a fastener actuator in a first position.
Figure 20B:
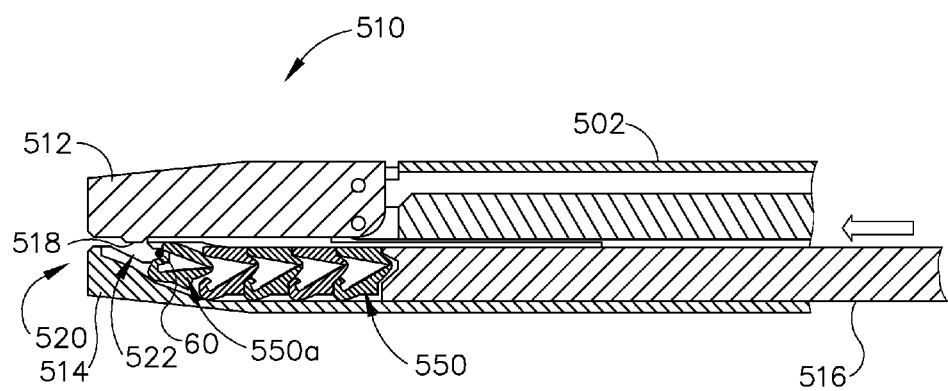
FIG. 20B depicts a side cross-sectional view of the end effector of FIG. 19 with the fastener actuator advanced distally to a second position to transition a first fastener to a partially actuated configuration.
Figure 20C:
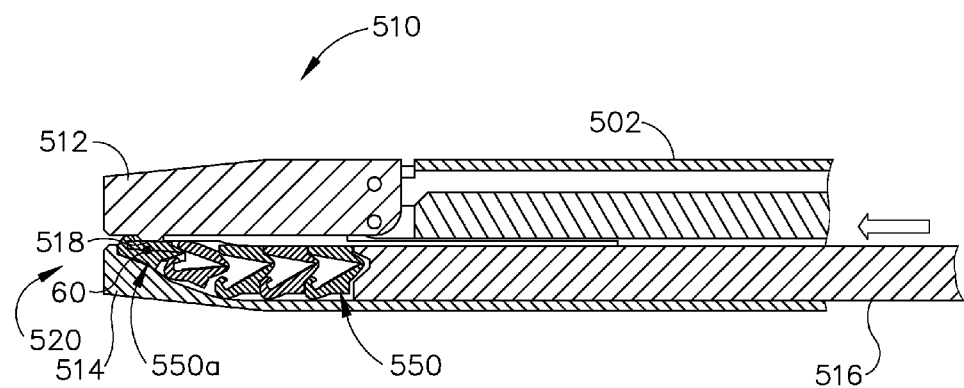
FIG. 20C depicts a side cross-sectional view of the end effector of FIG. 19 with the fastener actuator advanced distally to a third position to transition the first fastener to a fully actuated configuration.

VI. Exemplary Suture Fastening and Cutting Instrument with End-to-End Fastening Clips FIGS. 19-20C show yet another exemplary instrument (500) that is operable to apply fasteners (550) to strands (62, 64) of suture (60). Instrument (500) of this example includes a shaft (502) with an end effector (510) at the distal end of shaft. Shaft (502) and end effector (510) of the present example are sized and configured to fit through a conventional trocar for use in a minimally invasive surgical procedure, though it should be understood that shaft (502) and end effector (310) may have any other size and configuration. It should also be understood that numerous kinds of manual and/or automated control features may be provided at the proximal end of shaft (502) to control and drive end effector (510), including but not limited to those mentioned above in the context of instrument (100). Similarly, various kinds of components may be provided within shaft (502) to communicate motion to end effector (510), including but not limited to those mentioned above in the context of instrument (100). Various kinds of suitable components and features that may be provided within shaft (502) and at the proximal end of shaft (502) to operate end effector (510) will be apparent to those of ordinary skill in the art in view of the teachings herein.

End effector (510) of the present example includes a pivoting jaw (512) and a fastener applier (520) located within an interior region of a fixed jaw (514). Pivoting jaw (512) is operable to pivot toward and away from fixed jaw (514), in a manner similar to that described above with respect to jaw (112). Similarly, end effector (510) includes a translating cutter (not shown) that is operable similar to cutter (114) described above. Of course, as with any other pivotable jaw and cutter mentioned herein, jaw (512) and/or the cutter may be omitted if desired. Fastener applier (520) of the present example includes a slot (522) having a dogleg configuration. Slot (522) is in communication with a channel (524) that is formed in fixed jaw (514). As best seen in FIGS. 20A-20C, a plurality of fasteners (550) are positioned within channel (524) in an end-to-end configuration. A push rod (516) is positioned behind fasteners (550) and is operable to translate longitudinally to urge fasteners (550) distally as described below.

Figure 21A:
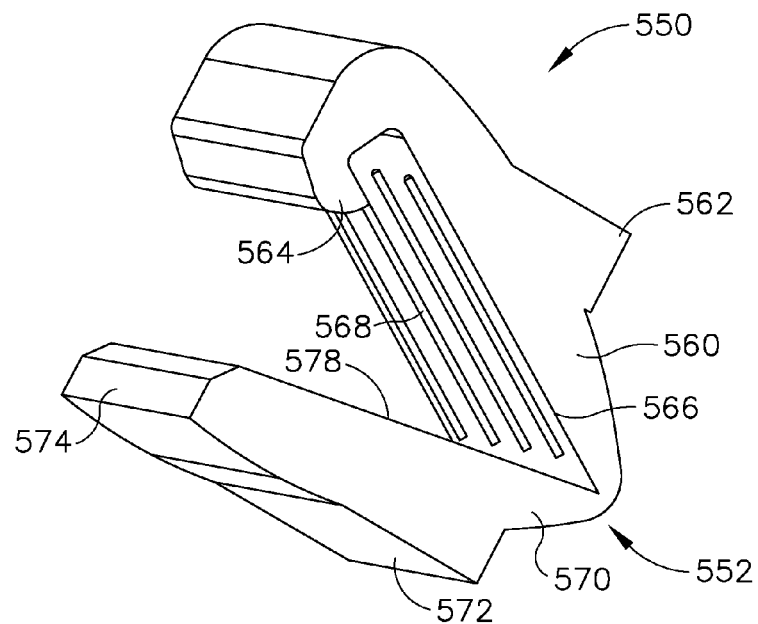
FIG. 21A depicts a perspective view of a fastener of the end effector of FIG. 19, in an open configuration.
Figure 21B:
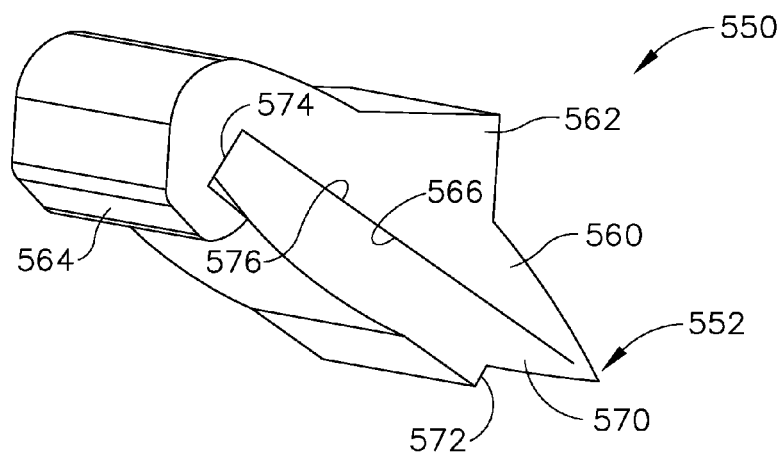
FIG. 21B depicts a perspective view of the fastener of FIG. 21A, in an actuated closed configuration.

21A-21B show fastener (550) in greater detail, including fastener (550) in an open position (FIG. 21A) and in a closed position (FIG. 21B). Fastener (550) of this example includes a living hinge (552) separating a first arm (560) from a second arm (570). First arm (560) includes a first protrusion (562), a retroflective clasp feature (564), and an inner face (566) having a series of protruding ribs (568). In some other versions, recesses, knurling, discrete round bumps, and/or other features are provided on inner face (566) in addition to or in lieu of ribs (568). Second arm (570) includes a second protrusion (572), a distal edge (574), and an inner face (576). Inner face (576) may include ribs, recesses (e.g., recesses complementing ribs (568) of opposing face (566)), knurling, discrete round bumps, and/or other features. Alternatively, inner face (576) may simply be substantially flat. Fastener (550) is configured to receive one or more suture strands between arms (560, 570) when fastener (550) is in the open position as shown in FIG. 21A.

As will be described below, end effector (510) is operable to close fastener (550) to the configuration shown in FIG. 21B, thereby securing the one or more strands of suture between arms (560, 570). Distal edge (574) fits within clasp feature (564) to substantially maintain fastener (550) in the closed configuration. It should be understood that clasp feature (564) and/or other features of fastener (550) may deform slightly during closure of fastener (550) to enable positioning of distal edge (574) in clasp feature (564). It should also be understood that ribs (568) and/or other features of faces (566, 576) may assist in securing the one or more strands of suture relative to the closed fastener (550). Other suitable components, features, and configurations for fastener (550) will be apparent to those of ordinary skill in the art in view of the teachings herein. It should also be understood that fastener (550) may be used in various other kinds of instruments; and that instrument (500) may use various other kinds of fasteners.

FIGS. 20A-20C depict a series of exemplary stages of use of instrument (500). It should be understood that instrument (500) may be used in cooperation with suturing instrument (10) at an incision in accordance with the various teachings herein, to secure a suture (60) relative to the incision to thereby provide one or more secure stitches at the incision. As shown in FIG. 20A, a suture (60) is disposed in slot (522), with jaw (512) being pivoted to a closed position adjacent jaw (514). While just a single strand of suture (60) is shown in slot (522) in this example, it should be understood that two or more strands of suture (60) may be disposed in slot (522). With a desired amount of tension being applied to suture (60) (e.g., using suturing instrument (10), etc.), push rod (516) is actuated distally. As shown in FIG. 20B, the interior sidewall of channel (524) narrows down to bear against arms (560, 570) of the distal-most fastener (550a), causing arms (560, 570) to close toward each other as distal-most fastener (550a) is urged distally by push rod (516). As push rod (516) is advanced further distally as shown in FIG. 20C, a cam feature (518) protruding from the underside of jaw (512) bears against arm (570) to drive distal edge (574) into clasp feature (564), thereby securing fastener (550a) in a closed configuration with suture (60) securely captured between arms (560, 570). Next, jaw (512) is pivoted away from jaw (514). As end effector (510) is then pulled away from the incision, fastener (550a) is pulled from end effector (510) by suture (60), which remains in the tissue. With the combination of fastener (550a) and suture (60) released from end effector (510), fastener (550a) secures suture (60) relative to the incision, just like any other fastener described herein, thereby securing one or more stitches at the incision. The above process may be repeated any desired number of times, advancing push rod (516) further distally each time, to secure any desired number of fasteners (550) to suture (60) to provide one or more additional stitches at the incision site.

VII. Exemplary Two-Stage Suture Fastening Instrument

Figure 22A:
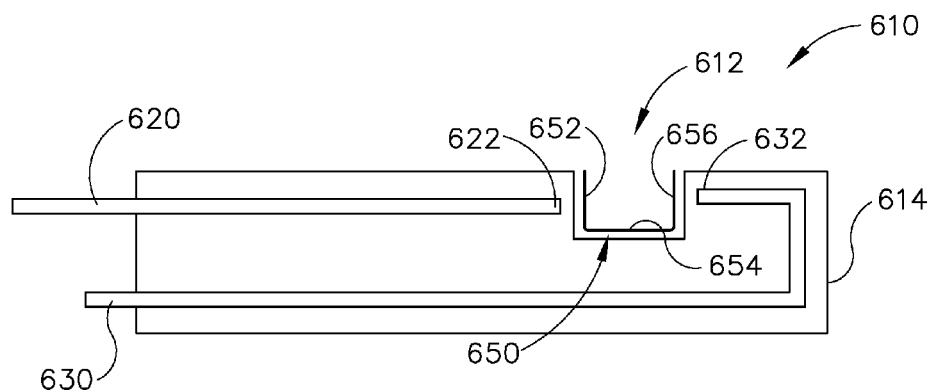
FIG. 22A depicts a side schematic view of another exemplary alternative end effector with first and second actuators positioned away from a fastener.
Figure 22B:
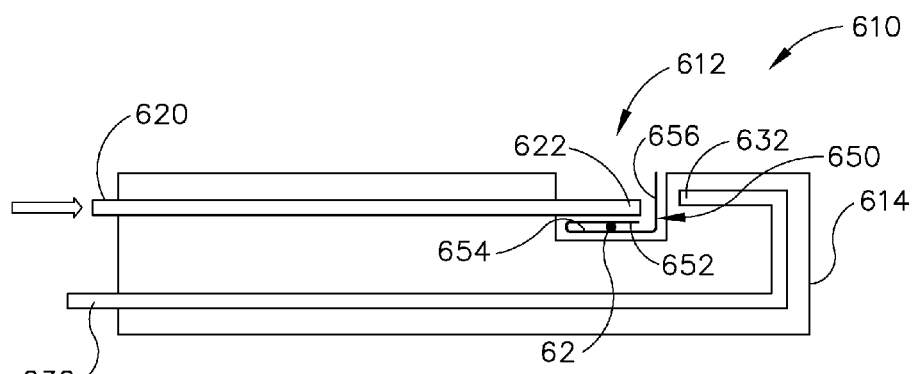
FIG. 22B depicts a side schematic view of the end effector of FIG. 22A with the first actuator advanced distally to partially actuate the fastener.
Figure 22C:
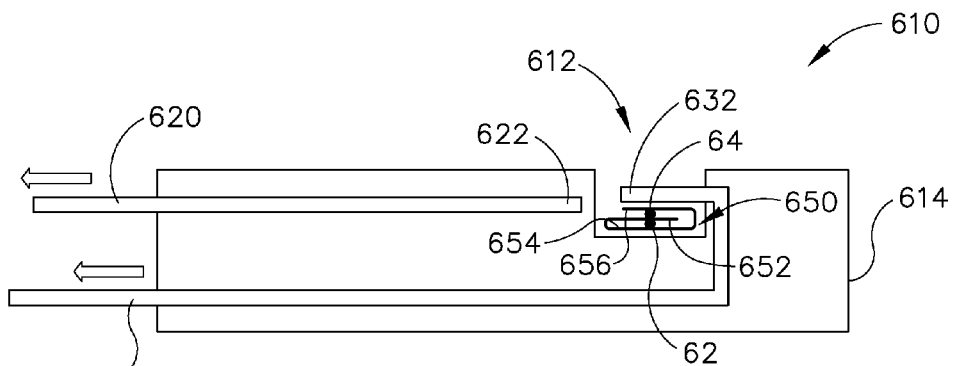
FIG. 22C depicts a side schematic view of the end effector of FIG. 22A with the first actuator retracted proximally and with the second actuator retracted proximally to fully actuate the fastener.

FIGS. 22A-22C show another exemplary end effector (610) that is operable to apply a fastener (650) to strands (62, 64) of suture (60). End effector (610) is positioned at the distal end of a shaft (not shown). The shaft and end effector (610) of the present example are sized and configured to fit through a conventional trocar for use in a minimally invasive surgical procedure, though it should be understood that the shaft and end effector (610) may have any other size and configuration. It should also be understood that numerous kinds of manual and/or automated control features may be provided at the proximal end of the shaft to control and drive end effector (610), including but not limited to those mentioned above in the context of instrument (100). Similarly, various kinds of components may be provided within the shaft to communicate motion to end effector (610), including but not limited to those mentioned above in the context of instrument (100). Various kinds of suitable components and features that may be provided within the shaft and at the proximal end of the shaft to operate end effector (610) will be apparent to those of ordinary skill in the art in view of the teachings herein.

End effector (610) of the present example includes a lateral notch (612) formed proximal to a closed distal end (614). While not shown, it should be understood that end effector (610) may also include a pivoting jaw (e.g., to grasp suture (60)) and/or a blade (e.g., to cut suture (60)), among various other optional features. A U-shaped fastener (650) is disposed in lateral notch (612). End effector (610) also includes a first actuator (620) and a second actuator (630). First actuator (620) is substantially straight and is longitudinally translatable such that a distal tip (622) of first actuator (620) may selectively enter and exit lateral notch (612). Second actuator (630) has a U-shaped distal end presenting a proximally projecting tip (632). Second actuator (630) is also longitudinally translatable such that a distal tip (632) of second actuator (630) may selectively enter and exit lateral notch (612).

It should be understood that end effector (610) may be used in cooperation with suturing instrument (10) at an incision in accordance with the various teachings herein, to secure a suture (60) relative to the incision to thereby provide one or more secure stitches at the incision. As shown in FIG. 22A, fastener (650) initially has a U-shaped configuration and rests in lateral notch (612), with actuators (620, 630) spaced away from lateral notch (612). One strand (62) of suture (60) is positioned within fastener (650) in lateral notch (612). First actuator (620) is then advanced distally, with distal tip (622) pushing one leg (652) of fastener (650) down onto strand (62) to thereby compress strand (62) between leg (652) and crown (654) of fastener (650) as shown in FIG. 22B. Next, first actuator (620) is retracted proximally to exit lateral notch (612) and another strand (64) of suture (60) is positioned on top of leg (652) in lateral notch (612). Second actuator (620) is then retracted proximally, with tip (632) pushing the other leg (656) of fastener (650) down onto strand (64) to thereby compress strand (64) between leg (654) and leg (652) of fastener (650) as shown in FIG. 22C. Fastener (650) is thus secured to both strands (62, 64) of suture (60). In some versions, fastener (650) is formed of a malleable material that substantially retains the configuration shown in FIG. 22C. In addition or in the alternative, fastener (650) may include one or more snap-lock features that help substantially retain the configuration shown in FIG. 22C. Various suitable forms that fastener (650) may take will be apparent to those of ordinary skill in the art in view of the teachings herein.

Once fastener (650) is secured to both strands (62, 64) of suture (60) as shown in FIG. 22C, second actuator (630) is advanced distally to exit lateral notch (612) to enable release of fastener (650) and suture (60) from lateral notch (612). In some versions, one or more features (e.g., cam features, spring-loaded features, etc.) assist in ejecting fastener (650) from lateral notch (612) upon distal advancement of second actuator (630) from the position shown in FIG. 22C. In addition or in the alternative, fastener (650) may simply be pulled away from lateral notch (612) by suture (60) when end effector (610) is pulled away from the incision. After fastener (650) and suture (60) are released from lateral notch (612), another fastener (650) may be loaded into lateral notch (612) and the above process may be repeated any desired number of times, to apply any desired number of additional fasteners (650) to suture (60) to provide one or more additional stitches at the incision site.

VIII. Exemplary Alternative Suture Fasteners

Figure 23A:
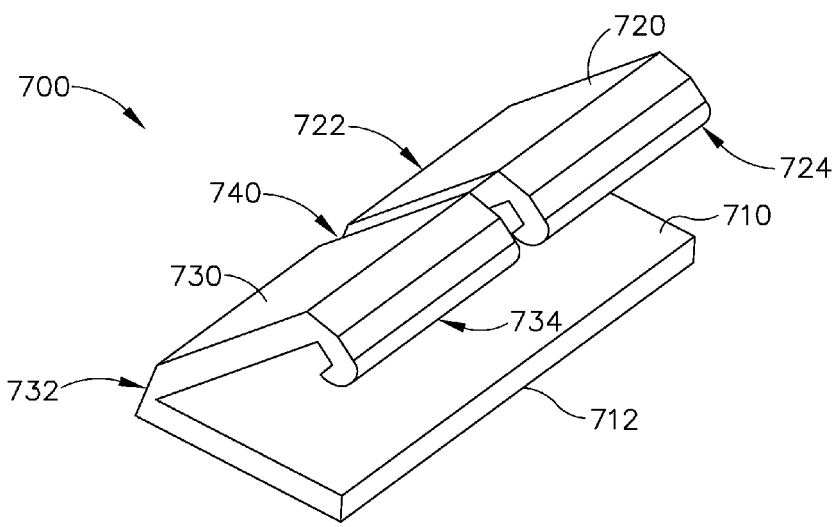
FIG. 23A depicts a perspective view of an exemplary alternative suture fastener in an open configuration.

FIGS. 23A-24B show exemplary alternative suture fasteners (700, 800) that may be used with one or more of the various end effectors described herein and/or with various other kinds of end effectors that will be apparent to those of ordinary skill in the art in view of the teachings herein. FIG. 23A shows fastener (700) in an open configuration while FIG.

23B shows fastener (700) in a closed configuration. Fastener (700) of this example comprises a base member (710), a first fastener member (720), and a second fastener member (730). Each fastener member (720, 730) is joined to base member (710) by a respective living hinge (722, 732). Living hinges (722, 732) are substantially collinear in the present example. Fastener members (720, 730) are also separated from each other by a gap (740). It should therefore be understood that fastener members (720, 730) may be pivoted relative to base member (710) independently from each other. Each fastener member (720, 730) includes a respective retroflective clasp feature (724, 734) similar to clasp feature (564) described above. Each clasp feature (724, 734) is configured to engage distal edge (712) of base member (710), similar to engagement between clasp feature (564) and distal edge (574) described above, to secure each fastener member (720, 730) in the closed position shown in FIG. 23B.

Figure 23B:
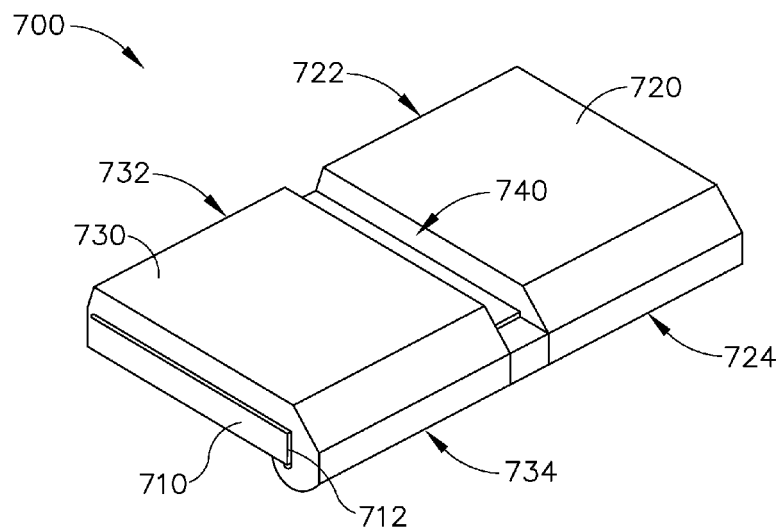
FIG. 23B depicts a perspective view of the suture fastener of FIG. 23A in a closed configuration.

It should therefore be understood that one or more strands of suture (60) may be positioned between one or both of fastener members (720, 730) and base member (710) when fastener members (720, 730) are in the open position as shown in FIG. 23A; and then one or both of fastener members (720, 730) may be pivoted to a closed position as shown in FIG. 23B to secure fastener (700) to suture (60). In some instances, a first strand (62) of suture (60) is secured by first fastener member (720) while a second strand (64) of suture (60) is simultaneously or subsequently secured by second fastener member (730). It should also be understood that one or both of fastener members (720, 730) may include one or more ribs (e.g., similar to ribs (568) described above), knurling, discrete round bumps, and/or other features that further assist in securing the position of fastener (700) on suture (60). Other suitable ways in which fastener (700) may be configured and operable will be apparent to those of ordinary skill in the art in view of the teachings herein.

Figure 24A:
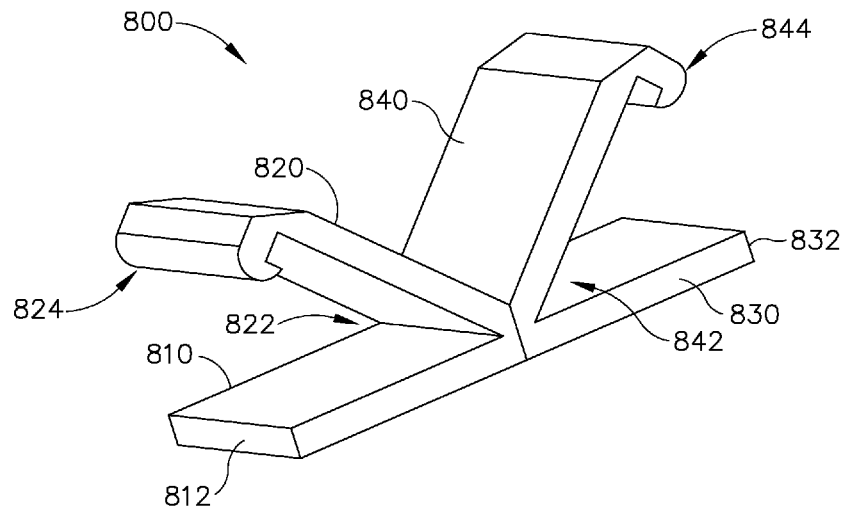
FIG. 24A depicts a perspective view of another exemplary alternative suture fastener in an open configuration.
Figure 24B:
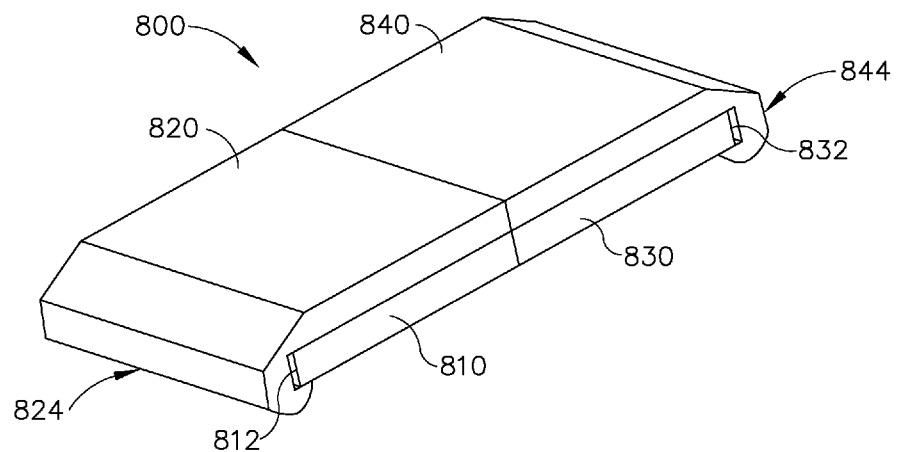
FIG. 24B depicts a perspective view of the suture fastener of FIG. 24A in a closed configuration.

FIG. 24A shows fastener (800) in an open configuration while FIG. 24B shows fastener (800) in a closed configuration. Fastener (800) of this example includes a first base member (810), a first fastener member (820), a second base member (830), and a second fastener member (840). Base members (810, 830) are substantially coplanar with each other in the present example and are joined unitarily together. Each base member (810, 830) has a respective outer edge (812, 832). Each fastener member (820, 840) is joined to the respective base member (810, 830) by a respective living hinge (822, 842). Living hinges (822, 842) are adjacent to each other in the present example, and separate fastener members (820, 840) to provide selective opening and closing of fastener members (820, 840) in opposing orientations. Fastener members (820, 840) are pivotable relative to the respective base members (810, 830) independently. Each fastener member (820, 840) includes a respective retroflective clasp feature (824, 844) similar to clasp feature (564) described above. Each clasp feature (824, 844) is configured to engage the corresponding outer edge (812, 832) of the corresponding base members (810, 830), similar to engagement between clasp feature (564) and distal edge (574) described above, to secure each fastener member (820, 840) in the closed position shown in FIG. 24B.

It should therefore be understood that one strand of suture (60) may be positioned between fastener member (820) and base member (810), and another strand of suture (60) positioned between fastener member (840) and base member (830), when fastener members (820, 840) are in the open position as shown in FIG. 24A. Fastener members (820, 840) may be pivoted to closed positions as shown in FIG. 24B to secure fastener (800) to suture (60). In some instances, a first strand (62) of suture (60) is first secured by first fastener member (820) and a second strand (64) of suture (60) is subsequently secured by second fastener member (840). It should also be understood that one or both of fastener members (820, 840) may include one or more ribs (e.g., similar to ribs (568) described above), knurling, discrete round bumps, and/or other features that further assist in securing the position of fastener (800) on suture (60). Other suitable ways in which fastener (800) may be configured and operable will be apparent to those of ordinary skill in the art in view of the teachings herein.

IX. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

While terms such as "clockwise" and "counterclockwise" have been used to describe directions of rotational movement during exemplary uses of instruments, it should be understood that these specific rotational directions are being provided only in reference to the examples depicted in the drawings. It is contemplated that rotational movement may be provided in directions opposite to those used above. Therefore, use of the terms "clockwise" and "counterclockwise" in any examples described herein should not be viewed as limiting in any way.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a shaft, wherein the shaft has a distal end;
   (b) an end effector disposed at the distal end of the shaft; and
   (c) a suture fastener removably secured to the end effector and defining a longitudinal axis, wherein the end effector is operable to selectively secure the suture fastener to a suture, wherein the suture fastener is configured to prevent the suture from being pulled through tissue, wherein the suture fastener comprises:
      (i) a first slit defining a first suture strand receiving feature; and
      (ii) a second slit defining a second suture strand receiving feature,
      wherein the first suture strand receiving feature is configured to receive and secure a first suture strand, wherein the second suture strand receiving feature is configured to receive and secure a second suture strand;
      wherein the first and second slits extend perpendicularly relative to the longitudinal axis of the suture fastener.

2. The apparatus of claim 1, wherein the shaft and end effector are both sized to fit through a trocar.

3. The apparatus of claim 1, wherein the end effector further comprises a pivoting jaw operable to selectively grasp a suture.

4. The apparatus of claim 3, wherein the end effector further comprises a fixed jaw, wherein the pivoting jaw is operable to pivot toward and away from the fixed jaw, wherein the suture fastener is disposed in the fixed jaw.

5. The apparatus of claim 4, wherein the fixed jaw includes an interior portion and an exterior portion, wherein the interior portion faces the pivoting jaw, wherein the suture fastener is disposed in interior portion of the fixed jaw.

6. The apparatus of claim 1, wherein the end effector further comprises a cutting member operable to sever a suture.

7. The apparatus of claim 1, wherein the end effector comprises a plurality of suture fasteners, wherein the end effector is operable to serially secure the suture fasteners to one or more sutures.

8. The apparatus of claim 7, wherein the plurality of suture fasteners are arranged in an end-to-end configuration.

9. The apparatus of claim 1, further comprising a suture fastener holder holding a plurality of suture fasteners, wherein the suture fastener holder is separate from the end effector, wherein the end effector is operable to load suture fasteners from the suture fastener holder.

10. The apparatus of claim 9, further comprising a suturing instrument, wherein the suturing instrument is operable to drive a needle and suture through tissue, wherein the suture fastener holder is attachable to the suturing instrument.

11. The apparatus of claim 1, wherein the suture fastener further comprises an inner fastener member and an outer fastener member, wherein the outer fastener member defines a bore configured to receive the inner fastener member, wherein the suture fastener is configured to capture one or more strands of suture between the inner fastener member and the outer fastener member.

12. The apparatus of claim 11, wherein the outer fastener member defines a lateral aperture configured to receive a strand of suture.

13. The apparatus of claim 11, further comprising a cartridge removably secured to the end effector, wherein the cartridge releasably holds the inner fastener member and the outer fastener member.

14. The apparatus of claim 1, wherein the end effector defines a slot configured to receive a strand of suture, wherein the end effector is operable to secure the suture fastener to a strand of suture positioned in the slot.

15. The apparatus of claim 1, further comprising one or more actuators operable to deform at least a portion of the suture fastener to thereby secure the suture fastener to a strand of suture.

16. An apparatus, comprising:
   (a) a shaft extending along a longitudinal axis, wherein the shaft has a distal end;
   (b) an end effector disposed at the distal end of the shaft; and
   (c) a plurality of suture fasteners disposed in one or both of the shaft or the end effector in an end-to-end configuration, wherein the plurality of suture fasteners extend along an axis that is parallel to but offset from the longitudinal axis, wherein the end effector is operable to serially secure the suture fasteners to one or more sutures, wherein each suture fastener is configured to prevent an associated suture from being pulled through tissue, wherein each suture fastener includes a first suture receiving portion and a second suture receiving portion, wherein each suture receiving portion is configured to be sequentially secured to one or more sutures.

17. An apparatus, comprising:
   (a) a shaft extending along a longitudinal axis, wherein the shaft has a distal end;
   (b) an end effector disposed at the distal end of the shaft; and
   (c) a suture fastener associated with the end effector, wherein the end effector is operable to selectively secure a first portion of suture to the suture fastener in a first stage of operation by inserting the first portion into a first opening of the suture fastener, wherein the end effector is further operable to selectively secure a second portion of suture to the suture fastener in a second stage of operation by inserting the second portion into a second opening in the suture fastener, wherein the suture fastener is configured to prevent the suture from being pulled through tissue;
   wherein the suture fastener comprises an inner fastener member and an outer fastener member, wherein the outer fastener member defines a bore configured to receive the inner fastener member, wherein the suture fastener is configured to capture one or more strands of suture between the inner fastener member and the outer fastener member, wherein the inner fastener member is configured to translate in a direction that is parallel to the longitudinal axis of the shaft.

* * * * *